US012668797B2

(12) United States Patent
Padron

(10) Patent No.: US 12,668,797 B2
(45) Date of Patent: Jun. 30, 2026

(54) COMPOSITIONS AND METHODS FOR TREATING CHRONIC MYELOMONOCYTIC LEUKEMIA

(71) Applicant: H. Lee Moffitt Cancer Center and Research Institute, Inc., Tampa, FL (US)

(72) Inventor: Eric Padron, Tampa, FL (US)

(73) Assignee: H. Lee Moffitt Cancer Center and Research Institute, INc., Tampa, FL (US)

( * ) Notice: Subject to any disclaimer, the term of this patent is extended or adjusted under 35 U.S.C. 154(b) by 1116 days.

(21) Appl. No.: 17/624,125

(22) PCT Filed: Aug. 21, 2020

(86) PCT No.: PCT/US2020/047357

§ 371 (c)(1),
(2) Date: Jul. 27, 2022

(87) PCT Pub. No.: WO2021/035128

PCT Pub. Date: Feb. 25, 2021

(65) Prior Publication Data

US 2023/0141661 A1 May 11, 2023

Related U.S. Application Data

(60) Provisional application No. 62/889,709, filed on Aug. 21, 2019.

(51) Int. Cl.

| | |
|---|---|
| ***C07H 21/02*** | (2006.01) |
| ***A61K 31/203*** | (2006.01) |
| ***A61K 31/573*** | (2006.01) |
| ***A61P 35/02*** | (2006.01) |
| ***C07H 21/04*** | (2006.01) |
| ***C12N 15/113*** | (2010.01) |

(52) U.S. Cl.

CPC .......... *C12N 15/113* (2013.01); *A61K 31/203* (2013.01); *A61K 31/573* (2013.01); *A61P 35/02* (2018.01); *C12N 2310/11* (2013.01)

(58) Field of Classification Search

CPC .......................... C12N 15/113; C12N 2310/11
See application file for complete search history.

(56) References Cited

U.S. PATENT DOCUMENTS 6,358,517 B1 * 3/2002 Pillai .................... A61Q 19/004 424/448
12,157,890 B2 * 12/2024 Freier ................ C12N 15/1135

FOREIGN PATENT DOCUMENTS

WO WO-2009075841 A2 * 6/2009 ......... A61K 31/4375
WO 2018191153 A1 10/2018

OTHER PUBLICATIONS

Stamato et al. (Cancer Research, 2017, 77(13 Supplement): Abs 2550).*
Balasis et al. (Blood, 2015, 126(23), 1641, 1-6).*
Ji et al. (PLoS One 8(11): e78700, 1-12).*
Elbashir et al. (The EMBO Journal, vol. 20, No. 23, pp. 6877-6888, 2001).*
Nedorezova et al. (Theranostics, 2022, vol. 12, Issue 16, 7132-7157).*
International Search Report received for PCT Application No. PCT/US2020/047357, mailed on Nov. 20, 2020, 4 pages.
Arber, et al., "The 2016 revision to the World Health Organization classification of myeloid neoplasms and acute leukemia", Blood, vol. 127, No. 20, May 19, 2016, pp. 2391-2405.
Arun, et al., "Differentiation of Mammary Tumors and Reduction in Metastasis upon Malat1 IncRNA Loss", Genes & Development, vol. 30, 2016, pp. 34-51.
Asami, et al., "Successful Treatment of Retinoic Acid Syndrome with High-Dose dexamethasone Pulse Therapy in a Child with Acute Promyelocytic Leukemia Treated with ATRA", Acta Paediatrica Japonica, vol. 37, 1995, pp. 384-387.
Bernard, et al., "Acute Promyelocytic Leukemia: Results of Treatment by Daunorubicin", Blood, vol. 41, No. 4, Apr. 1973, pp. 489-496.
Cambier, et al., "All-trans Retinoic Acid in Adult Chronic Myelomonocytic Leukemia: Results of a Pilot Study", Leukemia, vol. 10, 1996, pp. 1164-1167.
Cao, et al., "Resveratrol induces Apoptosis and Differentiation in Acute Promyelocytic Leukemia (NB4) Cells", Journal of Asian Natural Products Research, vol. 7, No. 9, Aug. 2005, pp. 633-641.
Fenaux, et al., "A Randomized Comparison of All Transretinoic Acid (ATRA) Followed by Chemotherapy and ATRA Plus Chemotherapy and the Role of Maintenance Therapy in Newly Diagnosed Acute Promyelocytic Leukemia", Blood, vol. 94, No. 4, Aug. 15, 1999, pp. 1192-1200.
Gast, et al., "Long Noncoding RNA MALAT1-derived mascRNA is involved in Cardiovascular Innate Immunity", Journal of Molecular Cell Biology, vol. 8, No. 2, Jan. 27, 2016, pp. 178-181.
Huang, et al., "Upregulation of Long non-coding Rna MALAT-1 Confers Poor Prognosis and Influences Cell Proliferation and Apoptosis in Acute Monocytic Leukemia", Oncology Reports, vol. 38, 2017, pp. 1353-1362.
Huarte, Maite, "The Emerging Role of IncRNAs in Cancer", Nature Medicine, vol. 21, No. 11, Nov. 5, 2015, pp. 1253-2161.

(Continued)

*Primary Examiner* — Amy Rose Hudson
(74) *Attorney, Agent, or Firm* — Pabst Patent Group LLP

(57) ABSTRACT

As disclosed herein, the long non-coding RNA (lncRNA) metastasis associated lung adenocarcinoma transcript 1 (MALAT1) is overexpressed and prognostic in Chronic Myelomonocytic Leukemia (CMML). MALAT1 depletion is disclosed herein as therapeutic strategy for treating CMML and other MALAT1 overexpressing leukemias. Also disclosed herein is a method of treating a subject with a leukemia that involves co-administering to the subject a MALAT1 silencing agent and a therapeutically effective amount of a differentiation agent, such as all-trans retinoic acid (ATRA).

7 Claims, 43 Drawing Sheets

(56) References Cited

OTHER PUBLICATIONS

Kim, et al., "Long noncoding Rna MALAT1 Suppresses Breast Cancer Metastasis", Nature Genetics, vol. 50, Dec. 2018, pp. 1705-1715.
Kong, et al., "The Ability of Endogenous Nras Oncogenes to initiate Leukemia is Codon-Dependent", Leukemia, vol. 30, Sep. 2016, pp. 1935-1938,.
Padron, et al., "An International Data Set for CMML Validates Prognostic Scoring Systems and Demonstrates a Need for Novel Prognostication Strategies", Blood Cancer Journal, vol. 5, Jul. 31, 2015, pp. 1-8.
Petrie, et al., "Differentiation Therapy of Acute Myeloid Leukemia: Past, Present and Future", Current Opinion in Hematology, vol. 16, 2009, pp. 84-91.
Puthanveetil, et al., "Long non-coding Rna MALAT1 Regulates Hyperglycemia induced Inflammatory process in the Endothelial Cells", Journal of Cellular and Molecular Medicine, vol. 19, No. 6, 2015, pp. 1418-1425.
Setty, et al., "Characterization of Cell Fate Probabilities in Single-Cell Data with Palantir", Nature Biotechnology, vol. 37, Apr. 2019, pp. 451-460.
Shi, et al., "Correlation of Increased MALAT1 Expression with Pathological Features and Prognosis in Cancer Patients: A Meta-Analysis", Genetics and Molecular Research, vol. 14, No. 4, Dec. 28, 2015, pp. 18808-18819.
Starczynowski, et al., "Identification of miR-145 and miR-146a as Mediators of the 5q- Syndrome Phenotype", Nature Medicine, vol. 16, No. 1, Jan. 2010, pp. 49-58.
Tripathi, et al., "The Nuclear-Retained Noncoding Rna MALAT1 Regulates Alternative Splicing by Modulating SR Splicing Factor Phosphorylation", Molecular Cell, vol. 39, Sep. 24, 2010, pp. 925-938.
Uszczynska-Ratajczak, et al., "Towards a Complete Map of the Human Long Non-Coding RNA Transcriptome", Nature Reviews Genetics, vol. 19, Sep. 2018, pp. 535-548.
Wang, et al., "Quantitative Production of Macrophages or Neutrophils ex vivo using Conditional Hoxb8", Nature Methods, vol. 3, No. 4, Apr. 2006, pp. 287-293.
Wilson, et al., "Hematopoietic Stem Cells Reversibly Switch from Dormancy to Self-Renewal during Homeostasis and Repair", Cell, vol. 135, Dec. 12, 2008, pp. 11118-1129.

* cited by examiner

COMPOSITIONS AND METHODS FOR TREATING CHRONIC MYELOMONOCYTIC LEUKEMIA

CROSS-REFERENCE TO RELATED APPLICATIONS

This application is a National Stage of International Application No. PCT/US2020/047357, filed Aug. 21, 2020, which claims benefit of U.S. Provisional Application No. 62/889,709, filed Aug. 21, 2019, which is hereby incorporated herein by reference in its entirety.

STATEMENT REGARDING FEDERALLY SPONSORED RESEARCH OR DEVELOPMENT

This invention was made with Government Support under Grant No. CA216757 awarded by the National Institutes of Health. The Government has certain rights in the invention.

BACKGROUND

Chronic Myelomonocytic Leukemia (CMML) is a myeloid neoplasm characterized by clinical features that overlap Myelodysplastic Syndromes (MDS) and Myeloproliferative Neoplasms (MPN) which culminate in a complex and aggressive natural history. The incidence of CMML is approximately 0.4 per 100 000, comparable to that seen in other adult leukemias. However, its prevalence is lower because the median overall survival is only 34 months and no therapies exist that augment this dismal natural history. Next generation sequencing technology has implicated epigenetic, splicing, and cytokine signaling pathways in the pathogenesis of CMML by annotating the frequencies of recurrent somatic gene mutations. Although this has allowed for the development of genetic murine model systems and uncovered potentially targetable vulnerabilities, current gene-based CMML models do not fully recapitulate the disease and no genomically-based therapy has been approved or is in clinical development.

SUMMARY

As disclosed herein, the long non-coding RNA (lncRNA) metastasis associated lung adenocarcinoma transcript 1 (MALAT1) is overexpressed and prognostic in CMML. MALAT1 depletion is therefore disclosed herein as therapeutic strategy for treating CMML and other MALAT1 overexpressing leukemias.

Disclosed herein is a composition comprising a therapeutically effective amount of a MALAT1 silencing agent and a therapeutically effective amount of a differentiation agent. Also disclosed herein is a method of treating a subject with a MALAT1 overexpressing leukemias that involves co-administering to the subject a MALAT1 silencing agent and a therapeutically effective amount of a differentiation agent. The disclosed method can further involve treating the subject with a therapeutically effective amount of dexamethasone. In some embodiments, the subject has not and does not receive dexamethasone.

Vitamin A and related retinoids were the first compounds to show differentiating effects in cell culture, and all-trans retinoic acid (ATRA) was subsequently found to be highly effective in inducing remission in promyelocytic leukemia, a disease characterized by a translocation involving the retinoic acid receptor, RAR-alpha. Subsequently, other pathways have been exploited as targets for development of differentiating agents, including histone deacetylase (HDAC), DNA cytosine methyltransferase (CMT), and vitamin D signaling pathways. CMT can be targeted for example by both 5-azacytidine and decitabine. In some embodiments, the differentiation agent is a retinoid compound that binds and activates the retinoic acid receptor (RAR), such as all-trans retinoic acid (ATRA). In some embodiments, the differentiation agent is arsenic trioxide (ATO)

The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia. In some embodiments, the leukemia is a chronic leukemia. In some embodiments, the leukemia is an acute leukemia. In some embodiments, the leukemia is a myelomonocytic leukemia. In some embodiments, the leukemia is a CMML.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5A is a volcano plot of transcriptome: CMML monocytes vs normal. FIG. 5B shows MALAT1 expression in primary CMML BMNCs (n=38) vs normal (n=10). FIG. 5C shows MALAT1 expression, survival plot(s), including i): leukemia-free survival, n=39: high n=23, low n=16, and ii) overall survival, n=73: high n=28, low n=45. FIG. 5D shows MALAT1 levels with somatic mutation heatmap (n=88).

FIG. 6A shows Human evolutionary trajectory of HSC. FIG. 6B shows pseudotime ordering. FIG. 6C shows differentiation potential. FIG. 6D shows gene expression trends. FIG. 6E shows murine evolutionary trajectory. FIG. 6F shows pseudotime ordering. FIG. 6G shows differentiation potential. FIG. 6H shows gene expression trends. FIG. 6I shows C57BL/6 vs MALAT1-/- mice i) LSK numbers, ii) HSC numbers, iii) MPP1, iv) MPP2, v) MPP3, and vi) MPP4. FIG. 5J shows competitive transplant: C57BL/6 vs MALAT1$^{-/-}$ BM.

FIG. 7A shows Nras$^{Q61R/+}$ vs Nras$^{Q61R/+}$ MALAT1$^{-/-}$ HSC numbers. FIG. 7B shows immortalized Nras$^{Q61R/+}$ vs Nras$^{Q61R/+}$ Malat1$^{-/-}$ mouse cells +/−estrogen. FIG. 7C shows THP-1 WT vs NT vs MALAT1 KO cells CD11b/CD14 double positive: i) DMSO control and ii) differentiated with 1 μM ATRA for 96 h. FIG. 7D shows Nanostring i) THP-1 NT vs MALAT1 KO and ii) immortalized Nras$^{Q61R/+}$ vs Nras$^{Q61R/+}$ Malat1$^{-/-}$. FIG. 7E shows THP-1 xenografts: i) heterotopic tumor growth and ii) orthotopic hCD45 engraftment. FIG. 7F shows MALAT1 overexpression: rescue of differentiation phenotype.

FIG. 8A is a bar graph of Gr-1/Mac-1 double positive numbers from ATRA treated Nras$^{Q61R/+}$ vs Nras$^{Q61R/+}$ Malat1$^{-/-}$ transplanted mice. FIG. 8B shows lung infiltration from Nras$^{Q61R/+}$ vs Nras$^{Q61R/+}$ Malat1$^{-/-}$ transplanted mice: i) ratio Mature: Immature and ii) % Mature. FIG. 8C shows THP-1 cells: i) adhesion and ii) migration.

FIG. 9A shows an experimental Design. FIG. 9B shows a representative flow plot. FIG. 9C shows CD34 CD38 flow analysis.

FIG. 10A shows whole transcriptome RNA sequencing Heat map. FIG. 10B shows CREB signature. FIG. 10C is a Western blot of THP-1 WT, NT, MALAT1 KO: p-/total CREB. FIG. 10D shows immunofluorescent microscopy of THP-1 WT, MALAT1 KO: p-CREB. FIG. 10E shows RNA immunoprecipitation: CREB & MALAT1. FIG. 10F shows rescue of differentiation phenotype with CREB1 overexpression. FIG. 10G shows CREB/PP2A co-immunoprecipitation.

FIG. 10C shows MALAT1 expression in CMML bone marrow mononuclear cells with wildtype vs mutated genes grouped by gene class.

DETAILED DESCRIPTION

Figure 1:
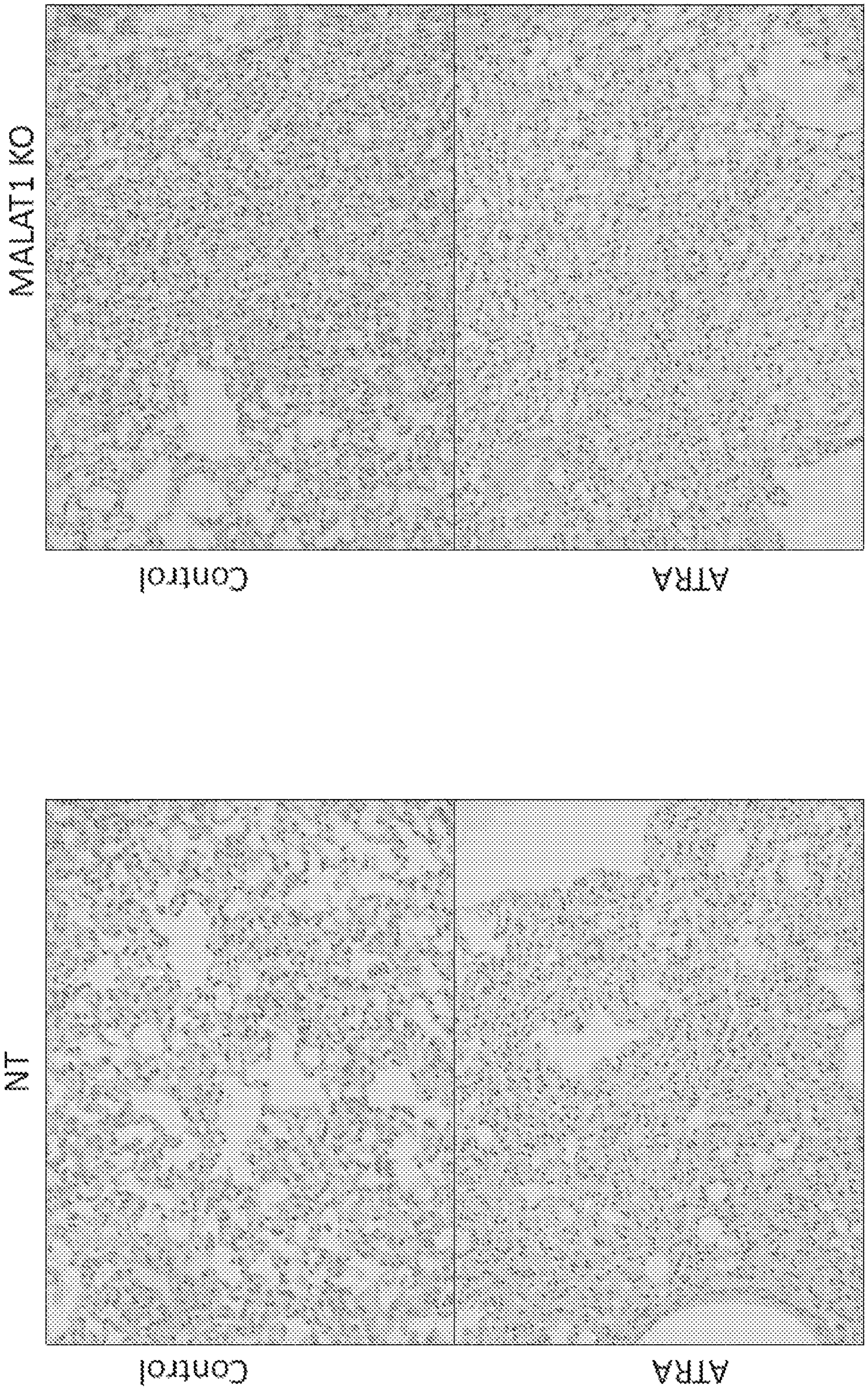
FIG. 1 shows evidence of differentiation syndrome in all-trans retinoic acid (ATRA) treated MALAT1 KO NSG xonografts.
Figure 2:
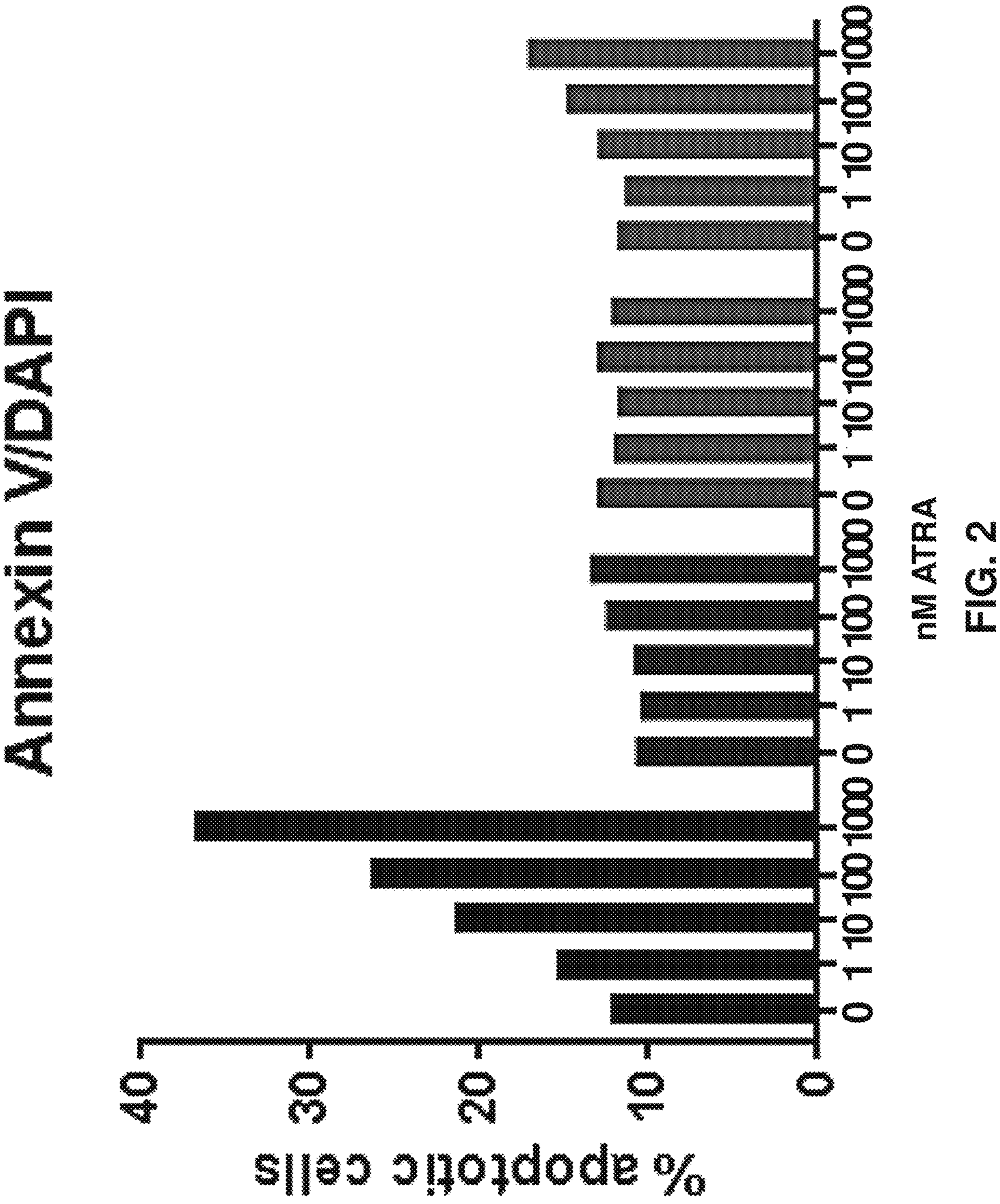
FIG. 2 shows minimal induction of apoptosis following ATRA treatment.
Figure 3:
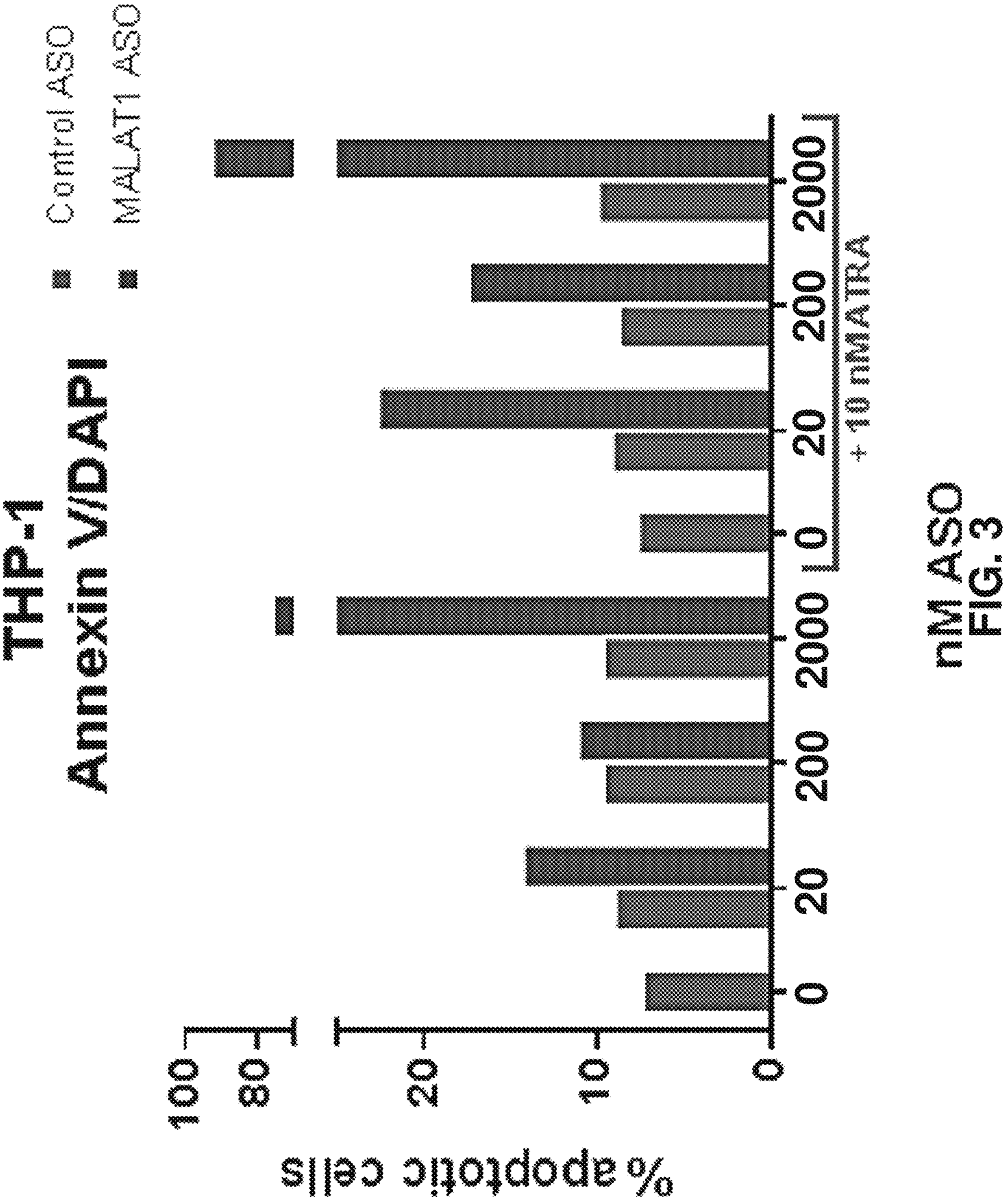
FIG. 3 shows MALAT1 ASO induces apoptosis in THP-1 cells and augments ATRA treatment.
Figure 4:
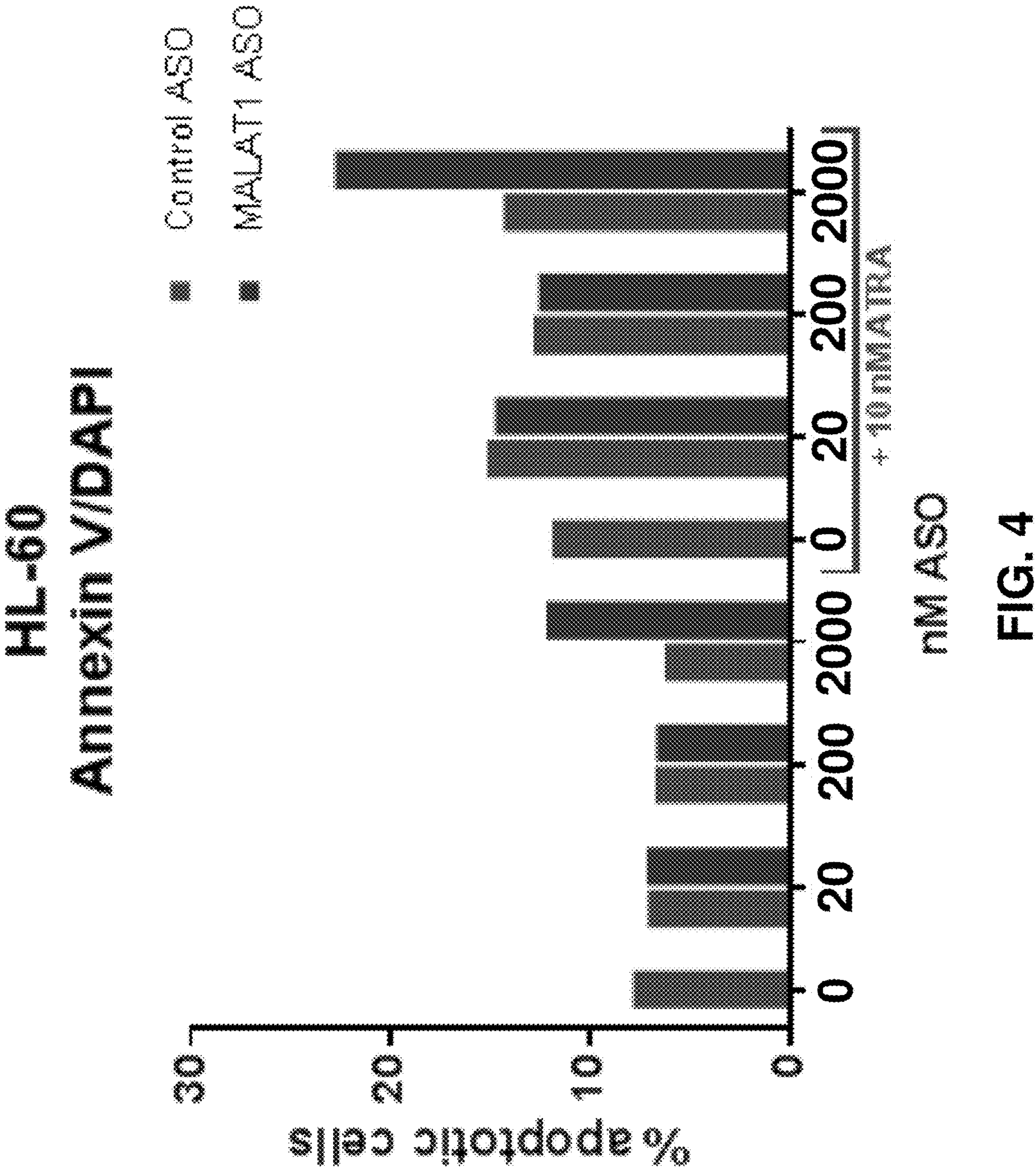
FIG. 4 shows MALAT1 ASO induces minimal apoptosis in HL-60 cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the term "retinoid" refers to any natural or synthetic compound that binds to the retinoic acid receptor ("RAR") and/or the retinoic X receptor ("RXR"). See, for example, Sporn and Roberts, Retinoids: Biology, Chemistry and Medicine," 01994 Lippincott Williams & Wilkins, Philadelphia, Pa., ISBN 978-0781700825, the content of which is incorporated herein by reference. The term "retinoid" explicitly includes, but is not limited to, ATRA, 13-cis RA, 9-cis RA, tazarotene, and the retinoids described in the following references: U.S. Pat. No. 4,666,941, U.S. Pat. No. 4,581,380, EP 0210929, EP 0232199, EP 0260162, EP 0292348, EP 0325540, EP 0359621, EP 0409728, EP 0409740, EP 0552282, EP 0584191, EP 0514264, EP 0514269, EP 0661260, EP 0661258, EP 0658553, EP 0679628, EP 0679631, EP 0679630, EP 0708100, EP 0709382, EP 0722928, EP 0728739, EP 0732328, EP 0749937, EP 0776885, EP 0776881, EP 0823903, EP 0832057, EP 0832081, EP 0816352, EP 0826657, EP 0874626, EP 0934295, EP 0915823, EP 0882033, EP 0850909, EP 0879814, EP 0952974, EP 0905118, EP 0947496, WO98/56783, WO99/10322, WO99/50239 and WO99/65872. Preferred retinoids include retinoic acid, all-trans retinoic acid, 13-cis-retinoic acid, 9-cis-retinoic acid, esters thereof, salts thereof, and metabolic precursors thereof.

A "retinoid" as the term is defined herein is also an agonist of one or both of RAR and/or RXR. Standard in vitro tests for receptor binding may be carried out to determine binding to RAR and RXR for any given retinoid. See, for example, Simoni, D. et al, (2001) "Retinoic Acid and analogs as potent inducers of differentiation and apoptosis. New promising chemopreventive and chemotherapeutic agents in oncology," Pure Appl. Chem. 73(9):1437-1444. RAR and RXR retinoid agonists, including both RAR-specific and RXR-specific agonists have been previously identified. In addition to the references noted earlier, see also WO 94/15902, WO 93/21146, WO 94/15901, WO 94/12880, WO 94/17796, WO 94/20093, WO 96/05165 and International Application No. PCT/US93/10166; European Patent Applications Nos. 87110303.2, 87309681.2 and EP 0718285; U.S. Pat. Nos. 4,193,931, 4,539,134, 4,801,733, 4,831,052, 4,833,240, 4,874,747, 4,879,284, 4,898,864, 4,925,979, 5,004,730, 5,124,473, 5,198,567, 5,391,569, Re 33,533, 5,693,493, 5,968,493, 6,030,964, 6,133,309, 6,147,244, and 6,593,493.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "agent" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an agent can be an oligomer of nucleic acids, amino acids, or carbohydrates including, but not limited to proteins, peptides, oligonucleotides, ribozymes, DNAzymes, glycoproteins, RNAi agents (e.g., siRNAs), lipoproteins, aptamers, and modifications and combinations thereof. In some embodiments, an active agent is a nucleic acid, e.g., miRNA or a derivative or variant thereof.

MALAT1 Silencing

MALAT1 targeting in preclinical cancer models has been mainly achieved by the use of synthetic oligonucleotides. Although MALAT1 is located in the nucleus, and therefore is less accessible than mRNAs to siRNAs, several studies have reported its successful knockdown by RNA interference approaches. Overall, inhibition of MALAT1 by siRNAs is achieved as the double-stranded RNA elicits a RISC-mediated degradation of the target lncRNA. In addition, antisense oligonucleotides (ASOs) represent a valuable approach to antagonize MALAT1. ASOs are small oligonucleotides with RNA/DNA-based structures that selectively bind to RNA via Watson-Crick hybridization, capable to cross the cell membrane, and to bind the target RNA in the nucleus as well as in the cytoplasm.

Advantages of ASOs over siRNAs include their independence on the RISC machinery, higher specificity and fewer off-target effects. Most of the ASOs are double-stranded oligonucleotides using the RISC complex to mediate the degradation of RNA, or single-stranded ASOs that inhibit RNA function through different mechanisms, such as alteration of RNA splicing, activation of RNase H which degrades the target RNA, inhibition of 5' cap formation and steric blockade of protein translation. Chemical modifications have been introduced to overcome some of the ASO constraints, like off-target/toxicity effects, high vulnerability to degradation by exo- and endonucleases, low affinity for the target, and poor delivery to the target tissues or low cellular uptake. These ASO modifications are defined as first generation and include a change in the phosphodiester with a phosphorothioate bond, the latter protecting the oligonucleotide from degradation and increasing the binding to receptor sites and plasma proteins; conversely, second-generation modifications refer to changes in the sugar moiety of the nucleobase increasing binding affinity to the target. The most relevant second-generation modification is the LNA (locked nucleic acid): this modification increases affinity, specificity and half-life determining effective delivery to target tissue with lower toxicity. Finally, the third generation ASOs include peptide nucleic acid (PNA) and phosphorodiamidate morpholino oligomer (PMO) reporting modifications to the furanose ring of the nucleotide. Depending on either the chemical modifications integrated into ASO or the type of inhibitory mechanism used, ASOs can be further divided in two main categories: mixmeRs and gapmeRs. In a mixmeR, LNA (locked nuclei acid) residues are dispersed throughout the ASO sequence, while gapmeRs contain a DNA or PS segment in the middle that promotes RNase H degradation of RNA target, flanked by LNAs.

The MALAT1-silencing agent may be any agent that inhibits MALAT1 expression or activity. Examples of silencing agents include antisense oligonucleotides, aptamers, siRNA, shRNA, sgRNA, miRNA, CRISPR (including CRISPR activation and CRISPR interference), TALENs, and Zinc Finger Nucleases.

In some embodiments, the MALAT1-silencing agent involves an antisense oligonucleotide (ASO), RNA interference (RNAi), siRNA, esiRNA, shRNA, miRNA, or a combination thereof.

In some embodiments, the MALAT1-silencing agent is an ASO described in U.S. Patent Application No. 2013/0225659, which is incorporated by reference in its entirety for the teaching of these ASOs.

In some embodiments, the MALAT1-silencing agent is an oligonucleotide described in U.S. Pat. No. 9,546,368, which is incorporated by reference in its entirety for the teaching of these oligonucleotides. In some embodiments, the MALAT-silencing agent is an In some embodiments, the MALAT1-silencing agent is an miR-101, miR-217, siRNA, or a combination thereof as described in Wang X, et al. J. Biol. Chem 2015 290&9): 3925-3935, which is incorporated by reference for the teaching of MALAT1-silencing agents.

Generally, ASOs that are effective in reducing the amount of expression of MALAT1 RNA in vivo can be used in the disclosed compositions and methods. ASOs targeted to the MALAT1 RNA comprise a specific antisense sequence that is complementary to a portion of the noncoding RNA transcribed from the target gene (i.e., the target RNA) and can be either DNA, RNA or a chemical analogue. ASOs are generally single-stranded (i.e. composed of an antisense strand, comprising the specific antisense sequence, only) and bind to the complementary portion of the target RNA.

Suitable ASOs have a length of from about 12 to about 35 oligonucleotides and any amount there between, and have sequence specificity (i.e., are complementary) to the MALAT1 noncoding RNA sequence. However, the ASOs of the present invention may compose more than about 35 oligonucleotides, for example, about 40, 50, 60, 70, 80, 90, 100, 110, 120, 130, 140, 150, 160, 170, 180, 190, 200, 210, 220, 230, 240, 250 oligonucleotides in length, or any number of oligonucleotides there between.

The specific antisense sequence comprised by an ASO can be identical or substantially identical to the complement of the target RNA sequence. In the context of the present invention, the specific antisense sequence comprised by the ASO molecule can be identical or substantially identical to the complement of the MALAT1 RNA sequence, that is, the complement of a contiguous portion of the RNA sequence.

The oligonucleotides employed as ASOs may be modified to increase the stability of the ASOs in vivo. For example, the ASOs may be employed as phosphorothioate derivatives (replacement of a non-bridging phosphoryl oxygen atoms with a sulfur atom) which have increased resistance to nuclease digestion (as done with ASO2 and ASO7). MOE modification (ISIS backbone) is also effective.

The ASOs may be prepared according to any of the methods that are well known to those of ordinary skill in the art. For example, the ASOs may be prepared by solid phase synthesis. See, Goodchild, J., Bioconjugate Chemistry, 1:165-167 (1990), for a review of the chemical synthesis of oligonucleotides. Alternatively, the ASOs can be obtained from a number of companies which specialize in the custom synthesis of oligonucleotides.

As is known in the art, the specificity of siRNA molecules is determined by the binding of the antisense strand of the molecule to its target RNA. Effective siRNA molecules are generally from 14 to 100 base pairs in length, or any length there between to prevent them from triggering non-specific RNA interference pathways in the cell via the interferon response, although longer siRNA can also be effective. For example, the siRNA molecules contemplated by the present invention may be 14, 15, 16, 17, 18, 19, 20, 21, 22, 23, 24, 25, 30, 35, 40, 50, 60, 70, 80, 90, 100 base pairs in length or any number of base pairs therebetween in length. Design and construction of siRNA molecules is known in the art (see, for example, Elbashir, et al., Nature, 411:494-498 (2001); Bitko and Bark, BMC Microbiol., 1:34 (2001)].

Suitable target sequences within the target RNA are selected using one or more of several criteria known in the art (see for example, Elbashir. S. M., et al. (2001) Nature 411, 494-498; Elbashir, S. M., et al. (2002) Methods 26, 199-213; Elbashir, S. M., et al. (2001) Genes Dev. 15, 188-200; Elbashir, S. M., et al. (2001) EMBO J. 20, 6877-6888; and Zamore, P. D., et al. (2000) Cell 101, 25-33). Target RNA sequences within the target RNA are typically between about 14 and about 50 nucleotides in length, or any length therebetween, but may be longer in length, for example, the target RNA sequence may be about 60, 70, 80, 90, 100, 110, 120, 130, 140, 150, 160, 170, 180, 190, 200, 210, 220, 230, 240, 250 base pairs in length, or any number of base pairs there between in length. The target RNA sequence can be selected from various regions within the MALAT1 RNA.

Following selection of an appropriate target RNA sequence, as described above, siRNA molecules that comprise a nucleotide sequence complementary to all or a portion of the target RNA sequence, i.e. an antisense sequence, can be designed and prepared. As indicated above, the siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. In one embodiment, the siRNA is a double-stranded siRNA. In another embodiment, the siRNA is a double-stranded siRNA wherein both RNA strands are the same length.

Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNA interference.

Small hairpin RNA (shRNA) molecules thus are also contemplated by the present invention. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). The spacer sequence is typically an unrelated nucleotide sequence that is situated between two complementary nucleotide sequence regions which, when annealed into a double-stranded nucleic acid, comprise a shRNA (see, for example, Brummelkamp et al., 2002 Science 296:550; Paddison et al., 2002 Genes Develop. 16:948; Paul et al., Nat Biotechnol 20:505-508 (2002); Grabarek et al., BioTechniques 34:734-44 (2003)). The spacer sequence generally comprises between about 3 and about 100 nucleotides.

The overall length of the siRNA molecules can vary from about 14 to about 100 nucleotides depending on the type of siRNA molecule being designed, and can be more than 100 nucleotides, such as, for example, about 14, 15, 16, 17, 18, 19, 20, 25, 30, 35, 40, 45, 50, 60, 70, 80, 90 100 nucleotides in length, or any number of nucleotides in length there between.

In an alternative embodiment, the siRNA molecule is a shRNA molecule or circular siRNA molecule between about 35 and about 100 nucleotides in length. In a further embodiment, the siRNA molecule is a shRNA molecule between about 40 to about 60 nucleotides in length.

As indicated above, the siRNA molecule comprises an antisense strand that includes a specific antisense sequence complementary to all or a portion of a target RNA sequence, such as, the MALAT1 noncoding RNA. One skilled in the art will appreciate that the entire length of the antisense strand comprised by the siRNA molecule does not need to be complementary to the target sequence. Thus, the antisense strand of the siRNA molecules may comprise a specific antisense sequence together with nucleotide sequences at the 5' and/or 3' termini that are not complementary to the target sequence. Such non-complementary nucleotides may provide additional functionality to the siRNA molecule. For example, they may provide a restriction enzyme recognition sequence or a "tag" that facilitates detection, isolation or purification. Alternatively, the additional nucleotides may provide a self-complementary sequence that allows the siRNA to adopt a hairpin configuration. Such configurations are useful when the siRNA molecule is a shRNA molecule, as described above.

Retinoic Acid

Generally, any retinoid compound that binds and activates the retinoic acid receptor (RAR) is useful in the methods of the present invention. More preferably, the retinoic acid compound is selected from the group consisting of all-trans-retinoic acid, 4-hydroxy-retinoic acid and 13-cis-retinoic acid. Most preferably, the retinoic acid compound is all-trans-retinoic acid. In some embodiments, the dose of the retinoic acid compound is between 10 nM and 1 μM.

A variety of retinoids and retinoid derivatives can be used in the disclosed compositions and methods. For example, retinol, retinal, all-trans-retinoic acid, 13-cis-retinoic acid, 13-trans-retinoic acid, and 9-cis-retinoic acid could all be used in the disclosed compositions and methods.

Retinoic acid (hereinafter "RA") has several different isomers and analogs. For example, all-trans retinoic acid (hereinafter "ATRA") has been formulated into a wide variety of pharmaceutical compositions by several manufacturers. In the United States, pharmaceutical compositions containing ATRA are generically designated "tretinoin." ATRA has the following structure:

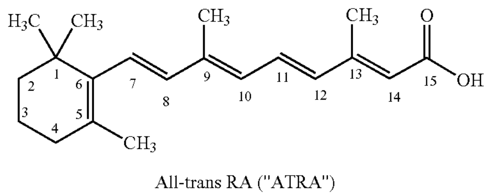 [SMILES: CC1=C(/C=C/C(C)=C/C=C/C(C)=C/C(=O)O)C(C)(C)CCC1]

All-trans RA ("ATRA")

The 13-cis version of retinoic acid is commonly referred to as "isotretinoin," and has the following structure:

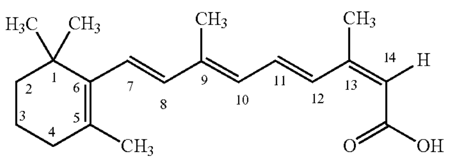

13-cis RA ("isotretinoin")

Isotretinoin is marketed in the United States under the trademark "ACCUTANE" (Hoffmann-La Roche, Inc., Nutley, N.J.).

The 9-cis version of retinoic acid is commonly referred to as "alitretinoin," and has the following structure:

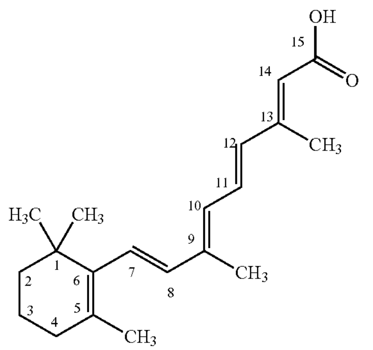

9-cis RA ("alitretinoin")

In some embodiments, the retinoid is a retinoid derivative, such as a derivative of 13-cis-retinoic acid, 13-trans retinoic acid, and 9-cis-retinoic acid. For example, retinoid derivatives are disclosed in U.S. Pat. No. 8,865,694, and U.S. Patent Publication No. 2011/0003892, are is incorporated by reference in their entireties for the teaching of these retinoid derivatives.

Derivatives of 13-cis-retinoic acid and 13-trans-retinoic acid useful in the invention are particularly described U.S. Pat. No. 4,885,311 and U.S. Pat. No. 5,124,356, both of which are incorporated herein by reference.

The RAR and RXR retinoid agonists referred to in the above-referenced patent applications, patents, and scientific articles may be used in the method described and claimed herein. Methods to make retinoids, dosage ranges, and suitable pharmaceutical compositions and formulations are described in the various patent applications/patents and scientific articles referred to above, all of which are incorporated herein by reference.

Pharmaceutical Compositions

Also disclosed herein are pharmaceutical compositions comprising one or more of the retinoids or pharmaceutically suitable forms thereof as described herein. More specifically, the pharmaceutical composition may comprise one or more of the retinoids as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, retinoids produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant retinoid(s).

For intravenous administration, the retinoid(s) may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative retinoid as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral, rectal, etc., as noted above) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the subject may be determined by one of ordinary skill in the art and depends upon various factors such as weight of the subject, age of the subject, immune status of the subject, etc., and is ultimately at the discretion of the medical or veterinary professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating central sleep apnea/hypopnea disorders in mammals, including humans, by administering an anti-central sleep apnea/hypopnea or obstructive sleep apnea effective amount of one or more the retinoids described herein. In particular, the compositions of the present invention may be used to treat central sleep apneas, hypopneas or obstructive sleep apnea of any and all description.

Administration

Administration of the therapeutic agents described herein can be carried out using the various mechanisms known in the art, including naked administration and administration in pharmaceutically acceptable lipid carriers. For example, lipid carriers for ASO delivery are disclosed in U.S. Pat. Nos. 5,855,911 and 5,417,978 which are incorporated herein by reference. The carrier may also be any one of a number of sterols including cholesterol, cholate and deoxycholic acid. In general, the therapeutic agents describe herein, including the ASOs and siRNA molecules, may be administered by intravenous, intraperitoneal, subcutaneous or oral routes, or direct local tumor injection.

Suitable formulations for parenteral administration include aqueous solutions of the therapeutic agents in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

In other embodiments, a therapeutic agent may be co-administered with an agent which enhances the uptake of the therapeutic agent by the cells. For example, a therapeutic agent may be combined with a lipophilic cationic compound which may be in the form of liposomes.

In addition, the therapeutic agents described herein may be conjugated to a peptide that is ingested by cells. Examples of useful peptides include peptide hormones, antigens or antibodies, and peptide toxins. By choosing a peptide that is selectively taken up by the cancerous prostate cells, specific delivery of the therapeutic agent may be effected.

The amount of a therapeutic agent administered in the present methods describe herein is one effective to reduce the amount of MALAT1 expression. It will be appreciated that this amount will vary both with the effectiveness of the ASO, siRNA or other therapeutic inhibiting agent employed, and with the nature of any carrier used. The determination of appropriate amounts for any given therapeutic agent is within the skill in the art, through standard series of tests designed to assess appropriate therapeutic levels.

The therapeutic agents described herein may also be administered as part of a pharmaceutical composition or preparation containing suitable pharmaceutically acceptable carriers comprising excipients and auxiliaries which facilitate processing of the therapeutic agents into preparations which can be used pharmaceutically.

Accordingly, the present invention contemplates pharmaceutical compositions comprising a therapeutic agent effective to reduce the amount of MALAT1 in cancerous cells exposed to the therapeutic agent, and a pharmaceutically acceptable carrier. The therapeutic agent may be an inhibiting agent of MALAT1, such as, for example, antisense oligonucleotides, RNA interference (RNAi), esiRNA, shRNA, miRNA, decoys, RNA aptamers, small molecule inhibitors, RNA/DNA-binding proteins/peptides or other compounds which inhibit the expression of MALAT1. In certain embodiments, the pharmaceutical composition may comprise one or more than one therapeutic agent, and a pharmaceutically acceptable carrier.

The pharmaceutical compositions used in the present invention include all compositions wherein the one or more than one therapeutic agent is contained in an amount which is effective to achieve inhibition of expression of MALAT1. While individual needs vary, determination of optimal ranges of effective amounts of each component is within the skill of the art.

The present invention further contemplates a method of treating cancer in a subject comprising the administration of a therapeutically effective amount of a MALAT1 silencing agent and retinoic acid in combination with any other treatment, agent, drug, regimen or therapy, including without limitation, hormonal therapy, surgery, radiation therapy, chemotherapy, biologic therapy, bisphosphonate therapy, cryosurgery, high-intensity focused ultrasound, and proton beam radiation therapy.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Credential the Therapeutic Candidacy of MALAT1 in Human CMML

Introduction

The long noncoding RNA (lncRNA) MALAT1 is overexpressed and associated with inferior overall survival in CMML. The purpose of this Example is to credential MALAT1 as a therapeutic target in this disease. This is accomplished by performing in vitro experiments that determine the effect of MALAT1 depletion (via CRISPR or antisense oligonucleotides (ASO)) on viability, proliferation, cell cycle, apoptosis, and differentiation. In vivo experiments are performed utilizing patient derived and cell-line derived xenografts, as well as genetically engineered models (GEM) of CMML to determine the phenotypic consequence of MALAT1 depletion on myelomonocytic leukemia.

Multiple MALAT1 depleted THP-1 leukemia cell line clones have been generated utilizing dual sgRNA-targeted CRISPR technology and partnered with IONIS pharmaceuticals to test clinical grade MALAT1 ASOs in a panel of cell lines. These reagents were used to evaluate the effects of MALAT1 depletion on the above cellular processes to include proliferation, cell cycle, and differentiation. An $NRAS^{Q61R/WT}$ CMML GEM murine model of CMML was successfully crossed with a $MALAT1^{KO/KO}$ mouse and utilized these models to evaluate the phenotypic consequence of MALAT1 depletion in vivo. Additionally, these models were used to test the impact of MALAT1 depletion on normal and leukemic stem cell self-renewal capacity as well as rigorously interrogated the numbers of hematopoietic stem and progenitor cells upon MALAT1 depletion. Leukemia human cell line xenograft models were used to test the in vivo consequence of MALAT1 depletion with the above CRISPR generated clones.

Results

CRISPR-generated human leukemia cell lines and MALAT1 ASO-treated cell lines were used to compare proliferation, cell cycle, viability, clonogenicity, and apoptosis, demonstrating no difference in these cellular processes when MALAT1 was depleted. However, when interrogating differentiation, there was a significant increase in differentiation markers CD11b and CD14 by flow cytometry which was enhanced when human leukemic cells were stimulated with phorbol myristate acetate (PMA) or all-trans retinoic acid (ATRA) in MALAT1 depleted versus control cells. This was also evident by morphologic assessment of differentiated cells. Importantly, while MALAT1 depletion or ATRA alone did not cause a robust dose-dependent apoptosis in myelomonocytic leukemia cell lines, the combination of ATRA and MALAT1 depletion induced apoptosis in a dose-dependent manner. These data suggest that depletion of MALAT1 in combination with ATRA maybe a viable therapeutic strategy in CMML. To determine whether this effect can be recapitulated in murine models of CMML, a HOXA8 driven in vitro differentiation model was generated (Wang, et al Nature Methods 2006) utilizing both NRAS$^{Q61R/WT}$ and NRAS$^{Q61R/WT}$/MALAT1$^{KO/KO}$ bone marrow cells. In this model, estrogen withdrawal leads to robust neutrophilic differentiation. However, NRAS$^{Q61R/WT}$/MALAT1$^{KO/KO}$ were observed to have increase differentiation markers even without estrogen withdrawal and a robust increase in differentiation compared to NRAS$^{Q61R/WT}$ upon withdrawal of estrogen by both differentiation markers and morphology.

When interrogating the in vivo GEM models of MALAT1 depletion and the CRIPSR human THP-1 leukemia MALAT1-depleted cell lines, two consistent phenotypic consequences were observed. First, reduced leukemic splenic and liver infiltration was identified in MALAT1 depleted models compared to controls in both xenografts and GEM models. Second, there was an inconsistent effect on survival in xenografts and a decreased survival in GEM models in which MALAT1 was depleted despite evidence of decreased leukemic infiltration within target organs. This effect was greatly enhanced in a pilot experiment in which our xenografts were additionally treated with ATRA. All MALAT1 depleted ATRA treated mice succumbed one-week post-ATRA therapy while controls (including ATRA treated WT xenografts) remained unaffected. Preliminary evidence suggests that these two observations may be explained by an in vivo differentiation syndrome preferentially occurring in MALAT1 depleted cells. Differentiation syndrome is a common serious adverse event in human leukemia patients treated with differentiating agents. It is primarily characterized by an inflammatory reaction often a result of differentiated myeloid cells accumulating in target organs, especially the lungs. Indeed, analysis of MALAT1 depleted mouse lung pathology demonstrates a robust infiltration of hematopoietic cells not seen in control mice.

Therefore, disclosed is the identification of MALAT1 depletion as a new differentiation therapy that can be enhanced by co-administration of ATRA. This represents a promising therapeutic strategy in CMML and perhaps other MALAT1 overexpressing leukemias.

Example 2: Determine the Effect of MALAT1 Depletion on CXCL8 and CXCL10

Introduction

MALAT1 depletion results in decrease of the chemokines CXCL8 and CXCL10, which are among the most overexpressed secreted proteins in CMML. This Example confirms that protein expression of these chemokines are down regulated in MALAT1 depleted cells and determines whether this occurs in an NFkB dependent manner using biochemical techniques to interrogate the physical interaction of this transcription factors at the chemokine promoter binding sites.

Multiple CRISPR MALAT1 depleted THP-1 clones (as above) have been generated that have a luciferase reporter for NFkB activity. These cells were stimulated with a variety of stimuli to include PMA and lipopolysaccharide (LPS) and NFkB activity was measured. RNA-sequencing experiments are used to determine the effects of MALAT1 depletion +/−ATRA therapy on downstream mRNA targets. Last, the hypothesis that MALAT1 acts as a molecular sponge sequestering and reducing the activity of key micro-RNAs (miRNAs) is explored (Tao, et al FASEB 2018). Two miRNAs were identified that are predicted to bind MALAT1 in mir145 and mir146a that are known to reduce NFkB activity (Starczynowski, et al Nat Med 2010). Reagents have been generated to interrogate the effects of MALAT1 depletion on these miRNAs and experiments are conducted to determine if reducing these miRNAs in MALAT1 depleted cells can rescue the differentiation phenotype.

Results

Utilizing CRISPR generated MALAT1 depleted NFkB reporter cell line clones, NFkB activity was tested across LPS and PMA doses confirming a decrease in NFkB activity upon MALAT1 depletion. This was additionally confirmed by decreases in CXCL8 and CXCL10 which are NFkB target genes. As mentioned above, miRNA binding prediction tools were used to identify mir145 and mir146a as potential MALAT1 targets. To confirm this, an RNA pull-down assay was performed that utilizes biotinylated MALAT1 ASO to enrich for miRNA species. Using this approach and using several controls (bead only, scramble ASO, WT and MALAT1 depleted cells), >1000-fold enrichment of both mir145 and mir146a was identified. A mir145 and mir146a reporter plasmid was generated that is transfected in both MALAT1 depleted and WT leukemic cells to determine if MALAT1 depletion augments miRNA activity. Additionally, several Locked Nucleic Acid (LNA) ASOs are obtained that deplete mir145 and mir146a, respectively. Using these, it is determined if miRNA depletion can rescue the differentiation phenotype seen in MALAT1 depleted cells. Last, an RNA-sequencing experiment is used to determine (4 replicates per group) the effects of MALAT1 depletion +/−ATRA treatment in our CRISPR generated cell lines.

As disclosed herein, MALAT1 depletion reduces NFkB activity, and two putative miRNAs have been identified that may be sequestered by MALAT1 and responsible for this effect.

Example 3: The Long Noncoding RNA MALAT1 Contributes to Differentiation Arrest in Human and Murine Monocytic Leukemia

Introduction

Chronic Myelomonocytic Leukemia (CMML) is a Myelodysplastic/Myeloproliferative neoplasm (MDS/MPN) characterized by cytopenias, marrow dysplasia, monocytosis, and a propensity for Acute Myeloid Leukemia (AML) transformation (Arber, D. A. et al. Blood 2016 127:2391-405). The median survival of higher risk CMML (i.e. CMML-2) is less than one year and is pathologically characterized by expansion of hematopoietic stem and progenitor cells (HSPC) within the bone marrow (Padron, E. et al. Blood Cancer 2015 J 5:e333). This differentiation arrest is ubiquitously associated with adverse outcomes and disease progression across myeloid neoplasms and defines transformation to AML when the bone marrow myeloblasts meet or exceed 20%. Several prognostic models for CMML and other myeloid neoplasms have demonstrated that incremental increases in the bone marrow myeloblast percentage is associated with inferior survival. The canonical master regulators of hematopoietic differentiation are generally thought to be a tightly regulated, limited set of transcription factors capable of directing hematopoiesis from pluripotency to terminal differentiation. Although several of these transcription factors critical for differentiation are mutated across a subset of myeloid neoplasms, the majority of cases do not harbor transcription factor mutations. Therefore, the molecular underpinnings governing differentiation arrest in the majority of myeloid neoplasms remain unexplored.

Long-noncoding RNAs (lncRNAs) are a functionally diverse class of transcripts that are greater than 200 nucleotides in length and do not code for proteins. Current annotations have estimated the existence of over 15,000 distinct lncRNAs suggesting comparable diversity to that of the protein-encoding transcriptome (Uszczynska-Ratajczak, B., et al. Nat Rev Genet 2018 19:535-548). Emerging data has recently implicated these molecules in the development and progression of a variety of malignancies suggesting that they play a pivotal role in oncogenesis (Huarte, M. Nat Med 2015 21:1253-61). Moreover, lncRNAs have also been implicated in critical cellular process, to include differentiation, that when dysregulated lead to manifestations of cancer hallmarks. MALAT1 is a highly conserved 8 Kb non-coding lncRNA enriched in the nucleus and thought to serve as a scaffold within the nuclear speckle where it associates with transcription factors and other regulatory elements (Tripathi, V. et al. Mol Cell 2010 39:925-38). MALAT1 is among the most well studied lncRNAs and has been associated with prognosis across a variety of solid tumors including lung adenocarcinoma, prostate adenocarcinoma, ovarian, and renal cell cancers (Shi, X. S. et al. Genet Mol Res 2015 14:18808-19). Depletion of MALAT1 in these tumors impairs cell proliferation, epithelial-mesenchymal transition (EMT), and metastasis in preclinical models (Tripathi, V. et al. PLoS Genet 2013 9:e1003368; Gutschner, T. et al. Cancer Res 2013 73:1180-9; Arun, G. et al. Genes Dev 2016 30:34-51). However, efforts to accurately model the oncogenic potential of MALAT1 have led to inconclusive in vivo results (Kim, J. et al. Nature Genetics 2018 50:1705-1715). These results have led some to postulate that the oncogenic effects of MALAT1 may be context or species specific because murine MALAT1 KO models do not display an overt malignant phenotype in contrast to what was expected based on the clear association between MALAT1 expression and solid tumors.

MALAT1 is overexpressed in inflammatory monocytes associated with cardiovascular innate immunity and its depletion impairs expression of TNF, IL6, CCRS, and CCR7 in this context (Gast, M. et al. J Mol Cell Biol (2016)). Other studies have demonstrated that glucose-dependent upregulation of TNF and IL6 are MALAT1 dependent triggering nuclear localization of β-catenin in endothelial cells (Puthanveetil, P., et al. J Cell Mol Med 2015 19:1418-25). Other than these observations, little is known regarding the consequence of MALAT1 expression among myeloid neoplasms and even less is known regarding its role in normal hematopoiesis. One retrospective study interestingly demonstrated that levels of MALAT1 were statistically higher in acute monocytic leukemia relative to other morphologic subtypes. Further, those acute monocytic leukemia patients with higher levels of MALAT1 had an inferior survival compared to those whose levels were below the median (Huang, J.-L. et al. Oncology reports 2017 38:1353-1362).

As disclosed herein, MALAT1 expression is increased and associated with inferior survival in CMML, even when correcting for known clinical and mutational prognostic variables. While MALAT1 depletion does not impact self-renewal capacity in normal or leukemic hematopoiesis, it is expressed highest in early hematopoietic stem cells and its depletion is associated with a decrease in the stem cell pool. Last, across several human and murine models of leukemia, MALAT1 depletion is associated with myelomonocytic differentiation and can be utilized as part of a therapeutic strategy aimed at terminally differentiating primary CMML cells.

Results

MALAT1 is overexpressed in CMML and is associated with inferior survival.

Figure 5A:
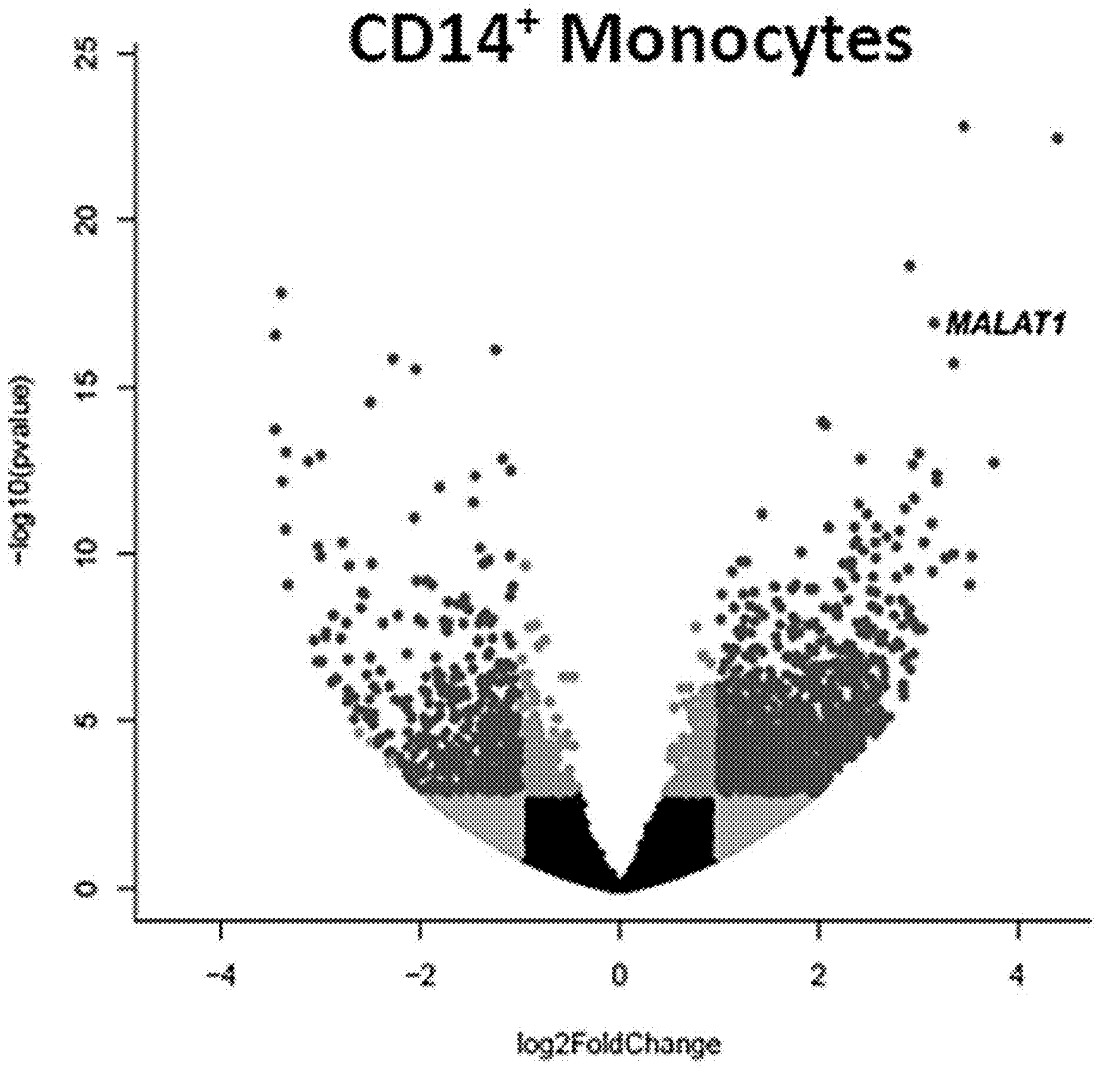
FIGS. 5A to 5D show MALAT1 is overexpressed in CMML and is associated with inferior survival.
Figure 5B:
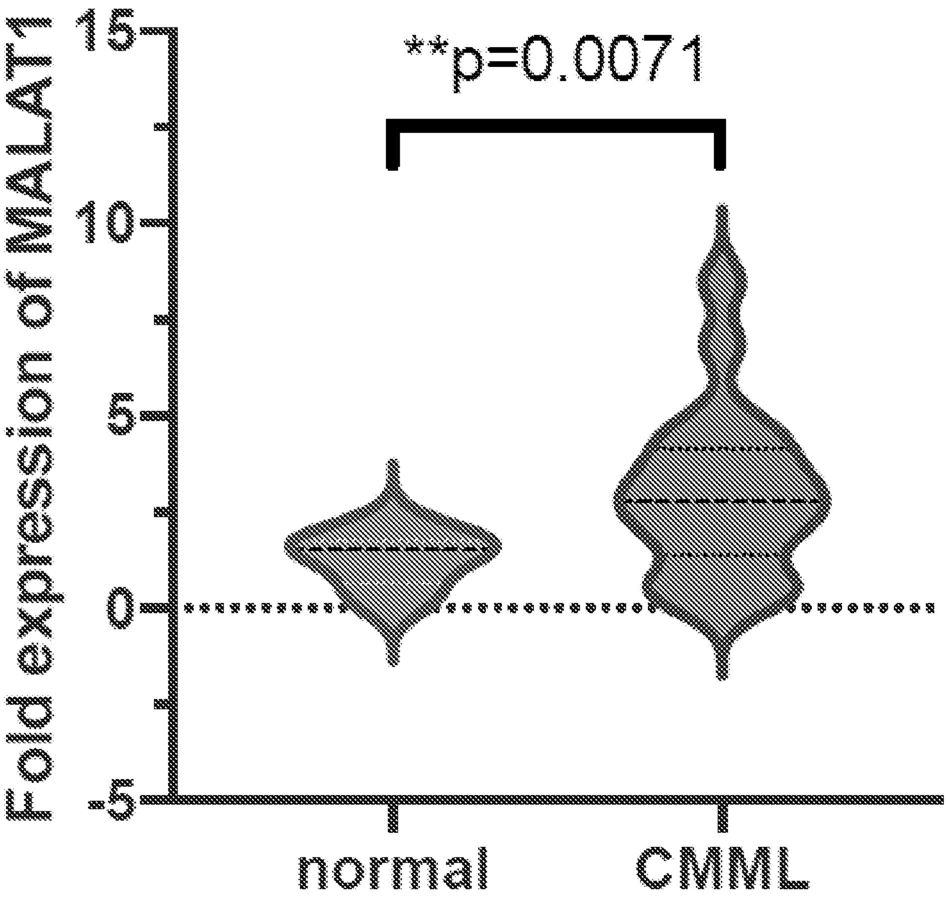
Figure 5C:
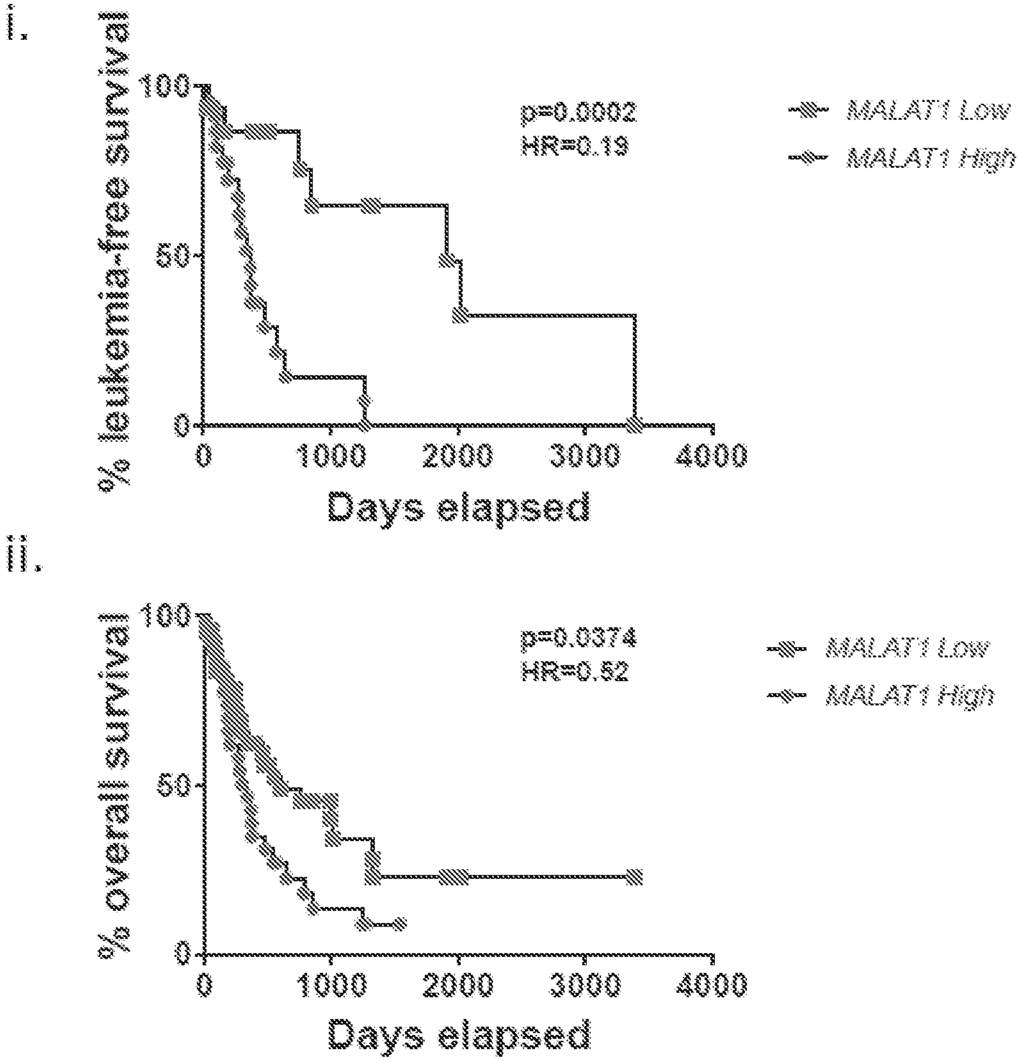
Figure 5D:
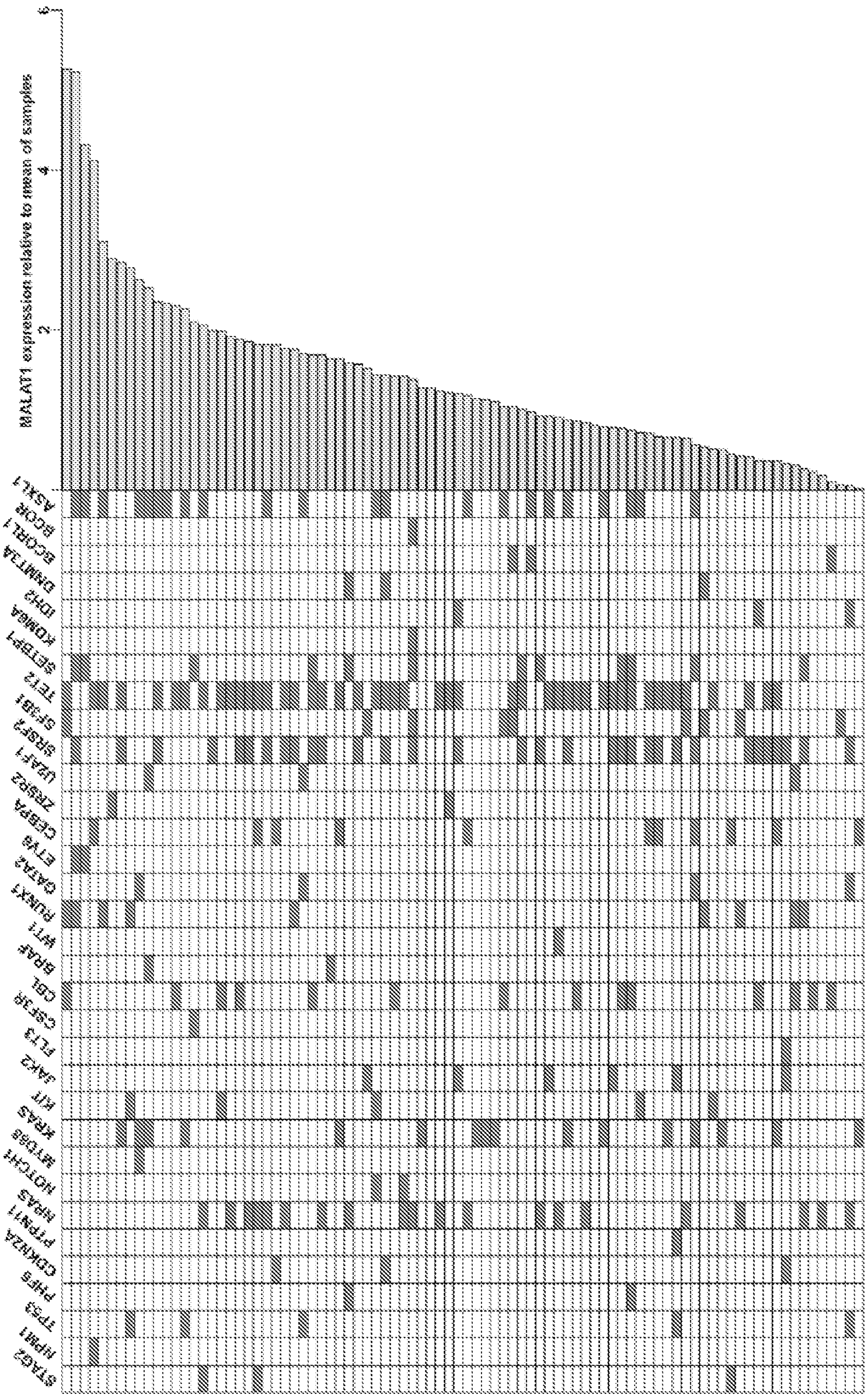
Figure 11B:
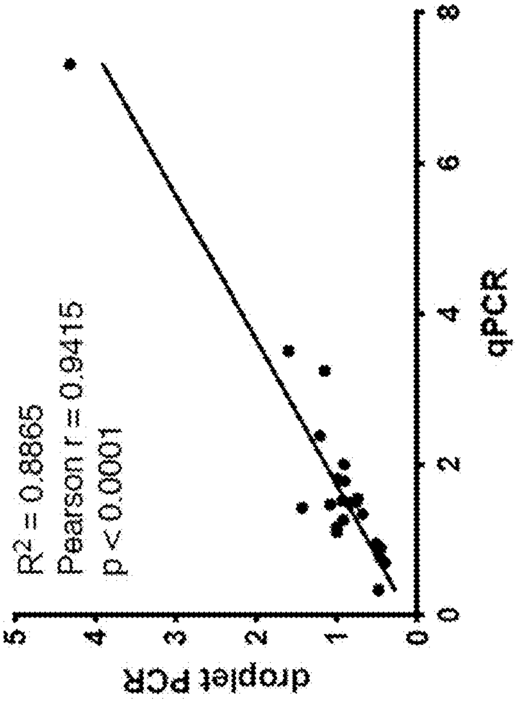
FIG. 11B shows digital droplet PCR vs qPCR of MALAT1 in CMML bone marrow mononuclear cells.
Figure 11A:
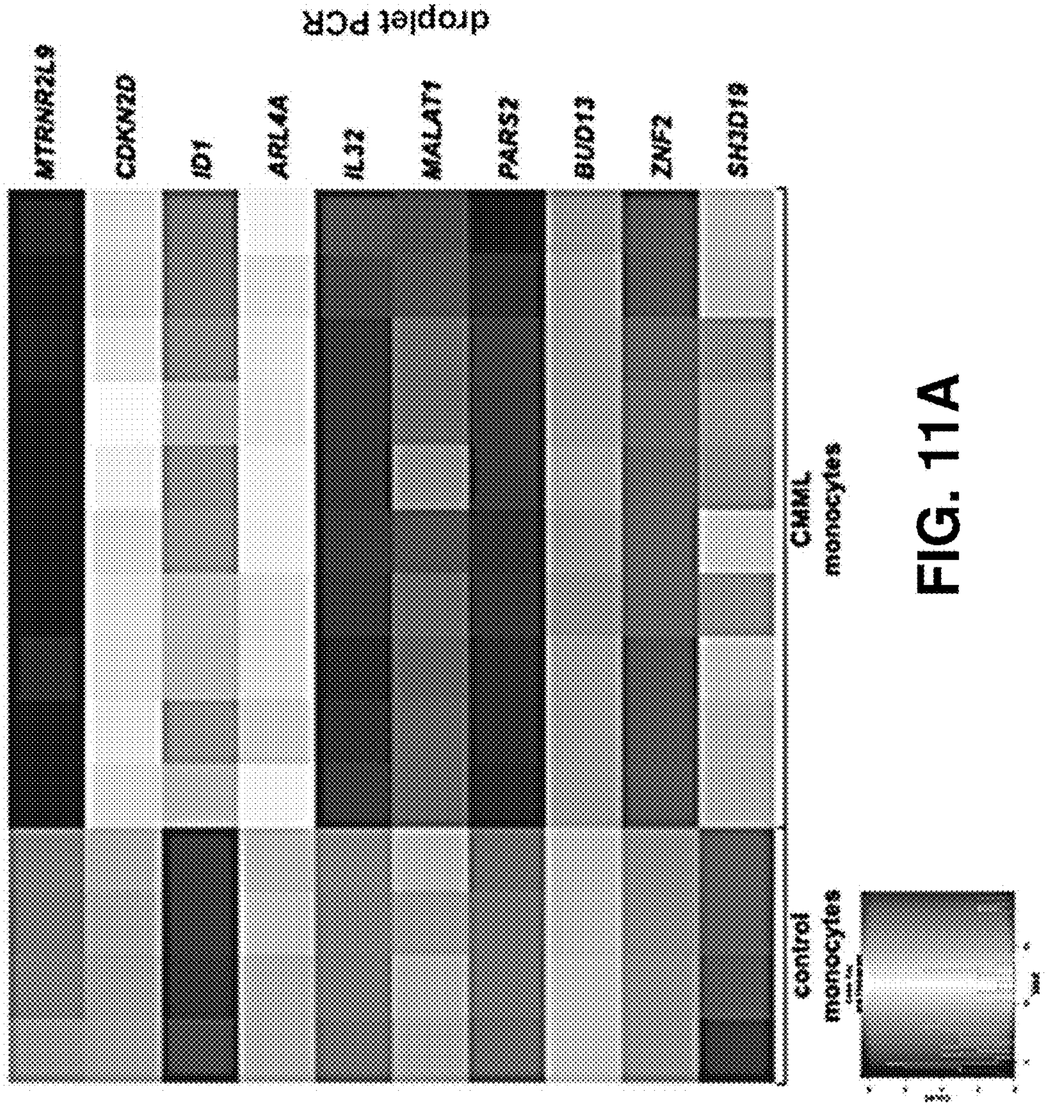
FIG. 11A is a heat map from RNA sequencing of CMML vs control monocytes showing the 10 most differentially expressed genes.
Figure 11C:
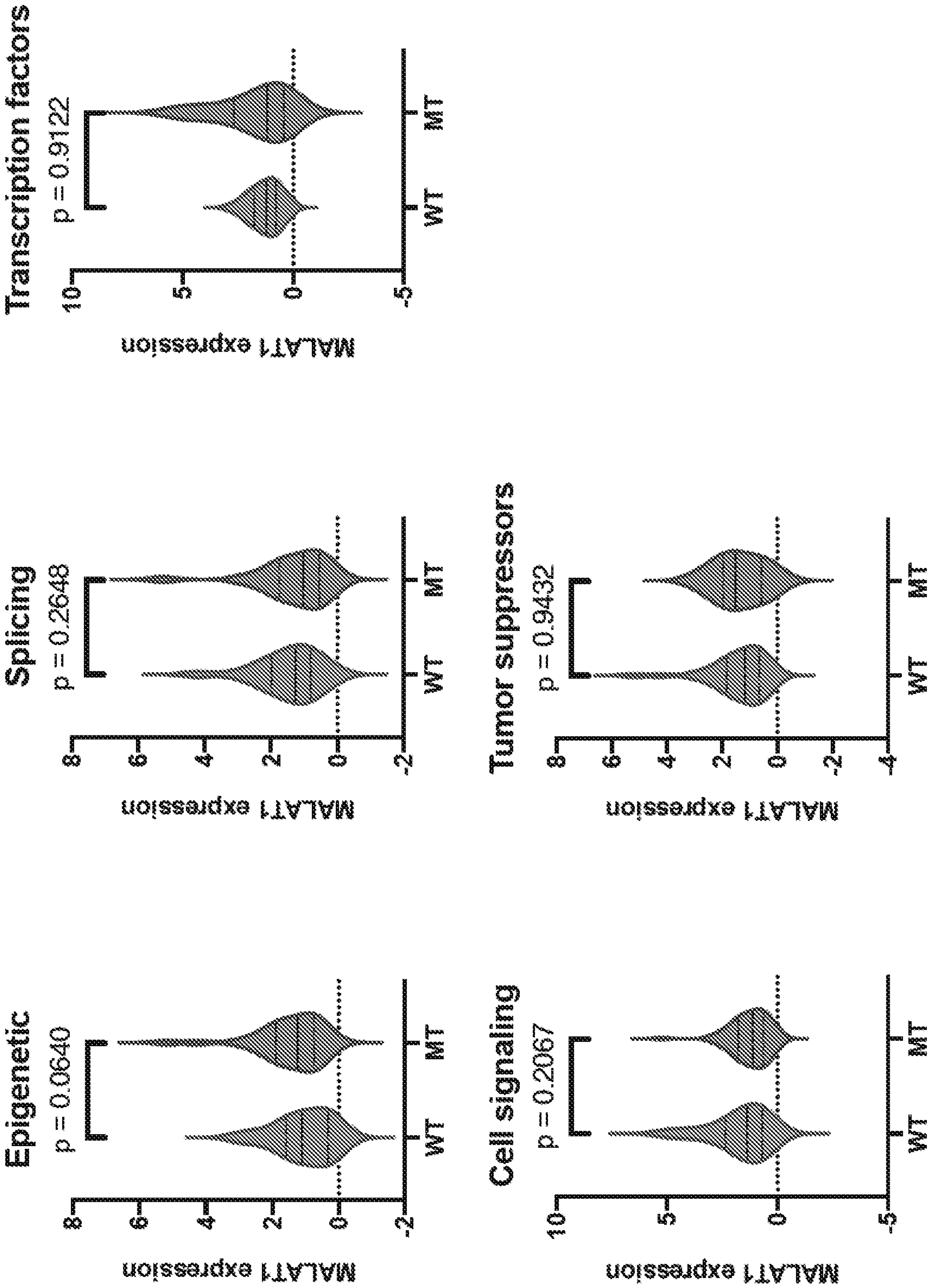

The expansion of human classical monocytes, defined as CD14+CD16$^-$, is a central hallmark of CMML. To nominate long noncoding RNAs significantly altered and potentially targetable in CMML, whole transcriptome RNA-sequencing of primary CMML peripheral monocytes (n=10) and control monocytes (n=4) was performed. The patient samples were retrieved at diagnosis and were representative of the entire clinical and genetic spectrum of the disease. Using a fold change of greater than 1.5 and FDR<0.05, lncRNAs that are significantly dysregulated in CMML monocytes were identified. Of these putative candidates, MALAT1 was the most differentially expressed transcript among lncRNAs and was the fourth highest differentially increased transcript across the entire coding and non-coding transcriptome (FIG. 5A). These results were validated by measuring MALAT1 levels in primary CMML bone marrow mononuclear cells (BMNCs) (n=73) and controls (n=12) utilizing both PCR and ddPCR which confirmed that, like peripheral blood monocytes, BMNCs from CMML patients had higher levels of MALAT1 (FIGS. 5B, 11A-11B). Further, CMML patients with MALAT1 levels twice the standard deviation of normal controls had an inferior overall survival when compared to those that did not even when corrected for known CMML prognostic scoring systems in multivariate analysis (n=73, 11.1 mo v 19.6 mo, Hazard Ratio=0.52 p=0.0374) (FIG. 5C). Interestingly, MALAT1 levels did not correlate with the presence or absence of any somatic mutation nor did it correlate with known clinical prognostic variables previously reported in CMML suggesting that MALAT1 overexpression is not genotype specific (FIG. 11C). Given this clinical and genetic data, it was concluded that MALAT1 is overexpressed and clinically relevant in human CMML and warranted further biological characterized.

MALAT1 is highly expressed and necessary for the maintenance of the hematopoietic stem cell pool.

Until recently, hematopoiesis has been modeled as a branching process defined by expression of surface proteins. However, single cell RNA sequencing (scRNA seq) technology now suggests that hematopoiesis arises via a probabilistic approach occurring through gradients of transcriptional differentiation (Setty, M. et al. Nat Biotechnol 2019 37:451-460; Buenrostro, J. D. et al. Cell 2018 173:1535-1548 e16). Using this modern framework, the expression of MALAT1 in human and murine hematopoiesis was examined. Although not polyadenylated, MALAT1 has an encoded polyA sequencing at its 3' end that can be leveraged by 3' capture scRNA seq methods such as 10× genomics. Given this and the relatively high cellular expression of MALAT1, it was reasoned that existing 10× hematopoietic datasets may inform MALAT1 expression across hematopoiesis.

Two datasets were used to evaluate hematopoiesis both the human and murine bone marrow mononuclear cell compartment. Both data sets were analyzed with the 10× analytical platform and then subjected to Palantir. Palantir is an algorithm that assigns a differentiation potential to each cell such that cells with a high differentiation potential are generally associated with expression of HSC markers and those with low differentiation potential are associated with terminal differentiation. Across human CD34+enriched cells and murine bone marrow mononuclear cells, MALAT1 was expressed highest in those cells with the highest differentiation potential and was both directly correlated to known HSC markers and inversely correlated to markers of terminal differentiation (FIGS. 6A-H, 12A-D).

Figure 6A:
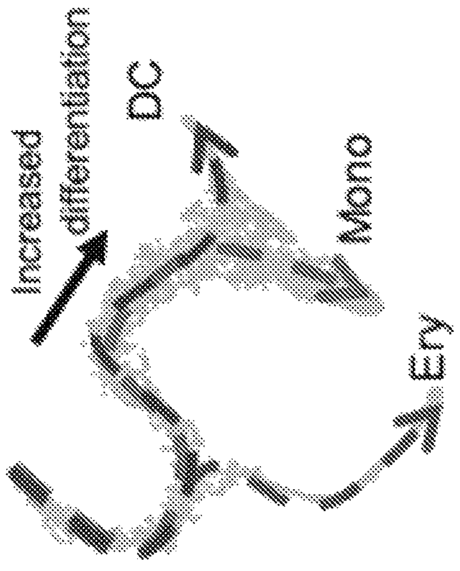
FIGS. 6A to 6J show MALAT1 is highly expressed and necessary for the maintenance of the hematopoietic stem cell pool.
Figure 6B:
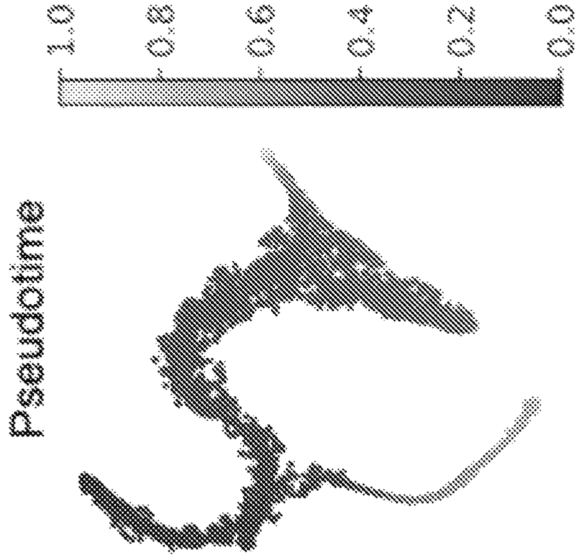
Figure 6C:
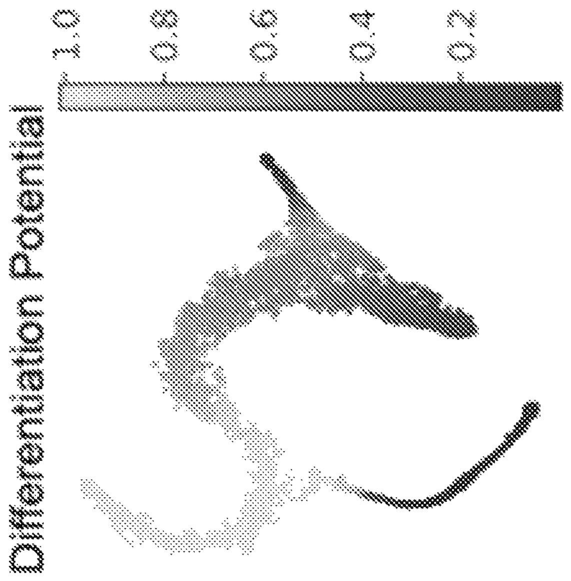
Figure 6D:
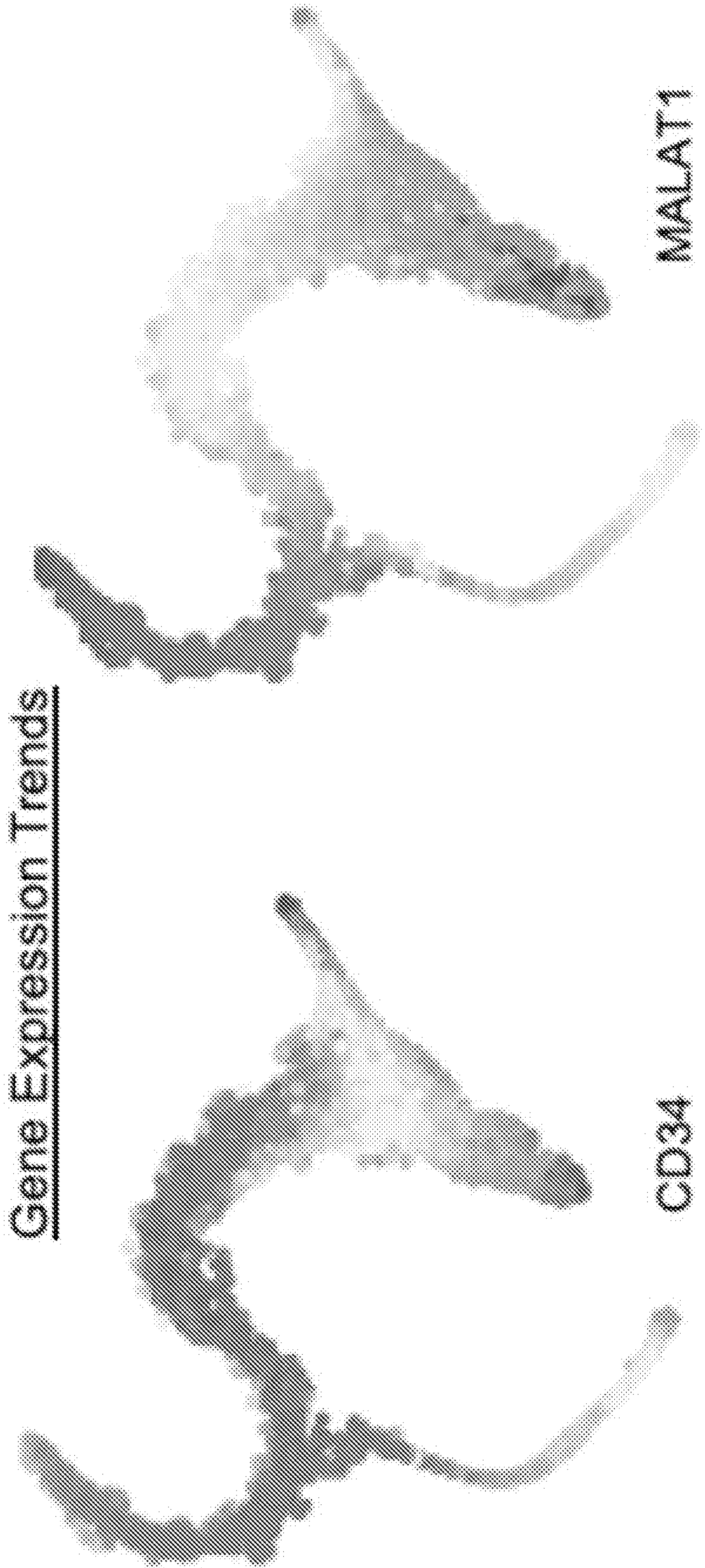
Figure 6E:
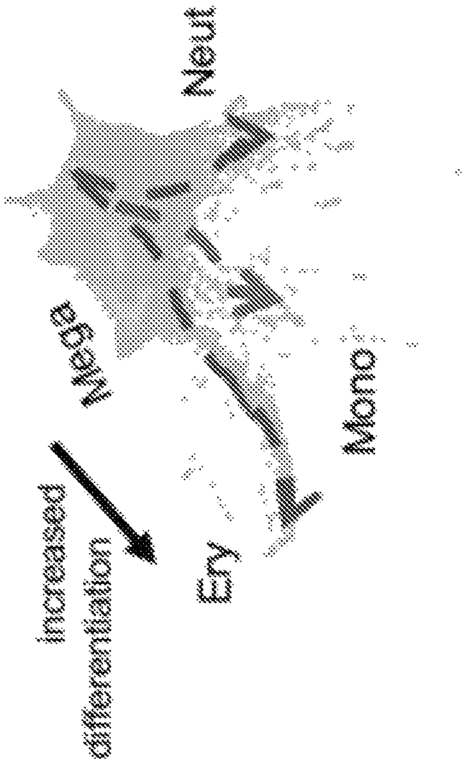
Figure 6F:
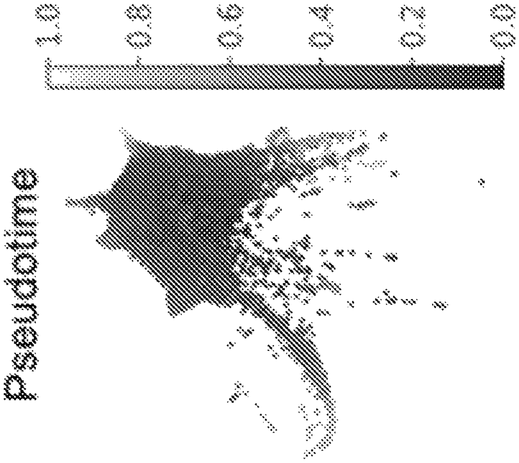
Figure 6G:
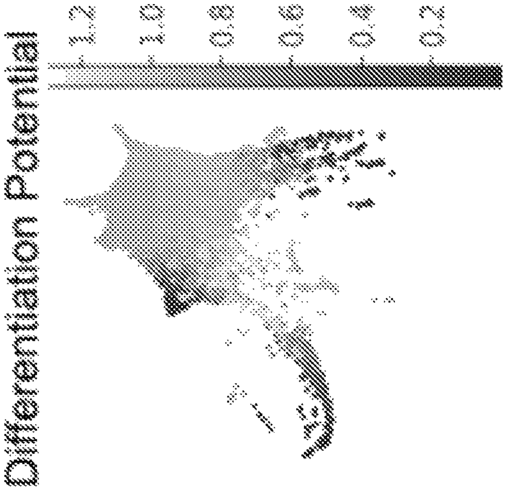
Figure 6H:
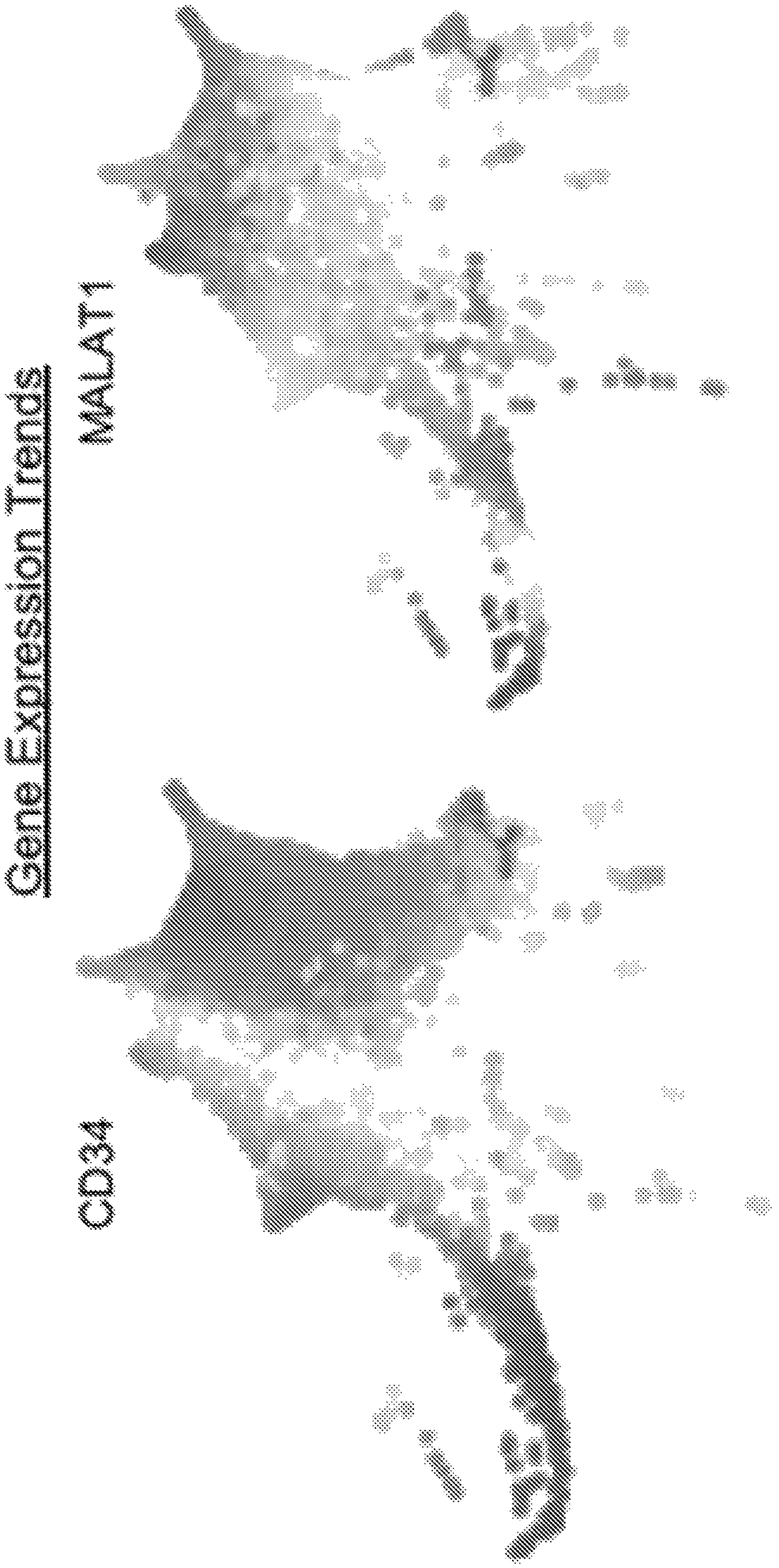
Figure 6I:
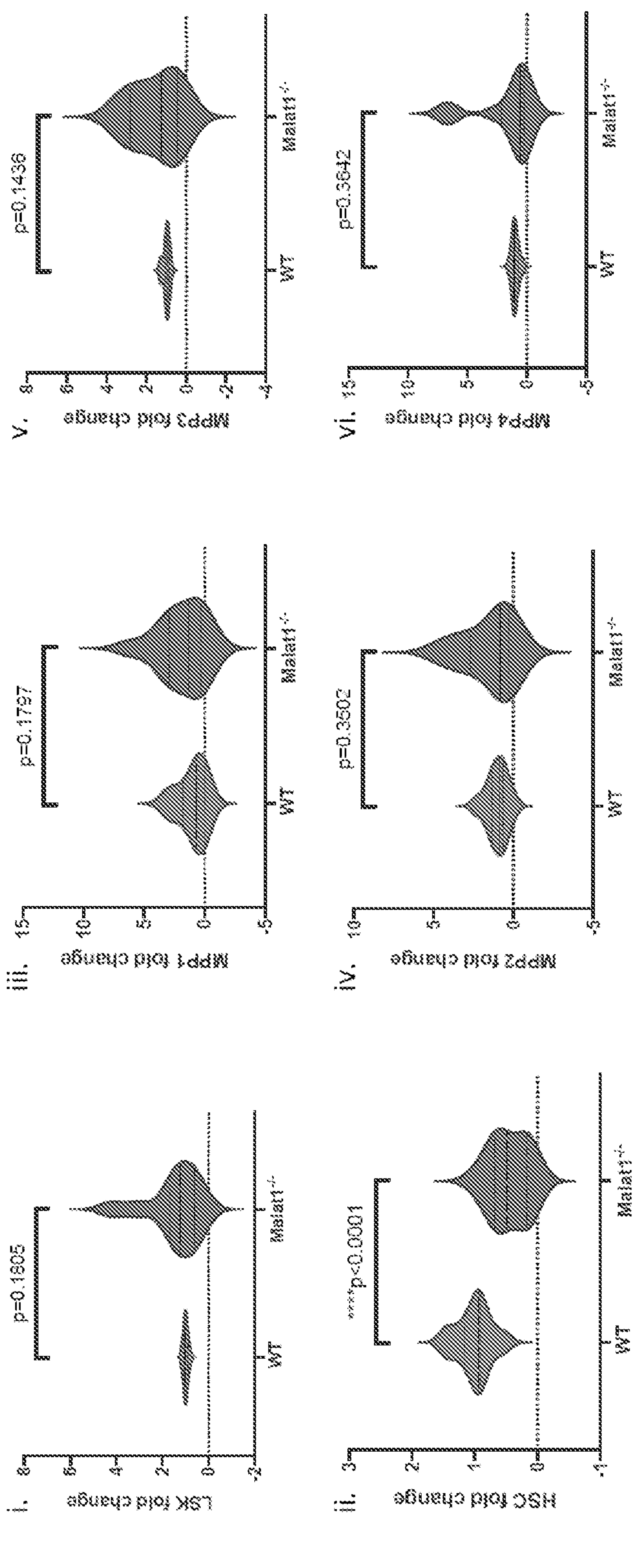
Figure 6J:
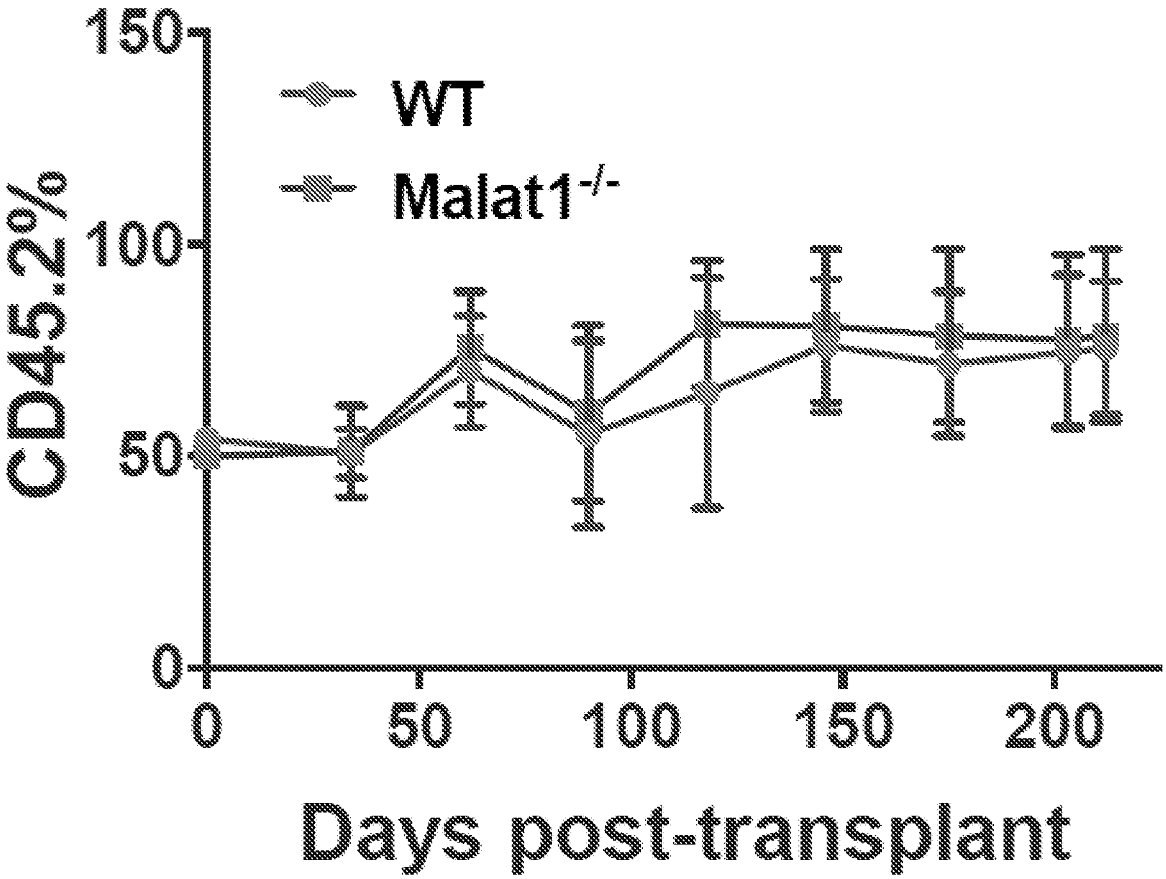
Figure 12A:
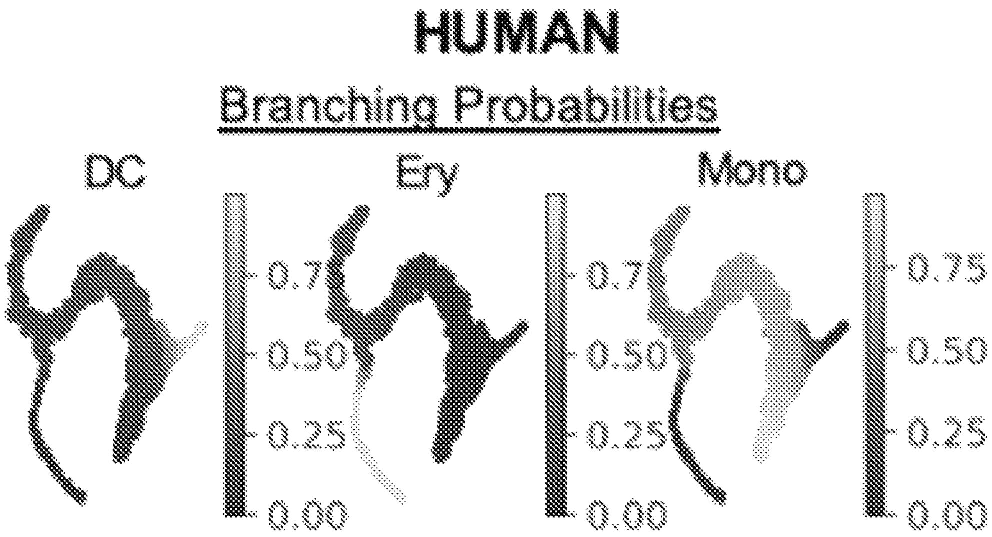
FIG. 12A shows human individual branching probabilities.
Figure 12B:
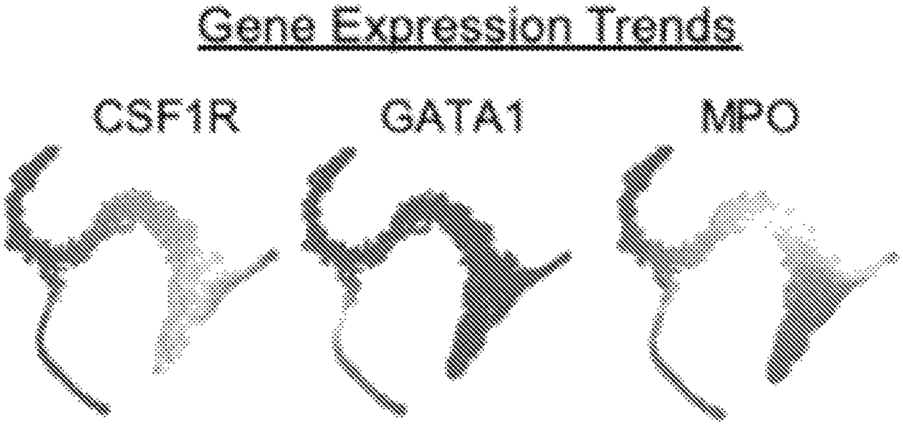
FIG. 12B shows additional human gene expression trends.
Figure 12C:
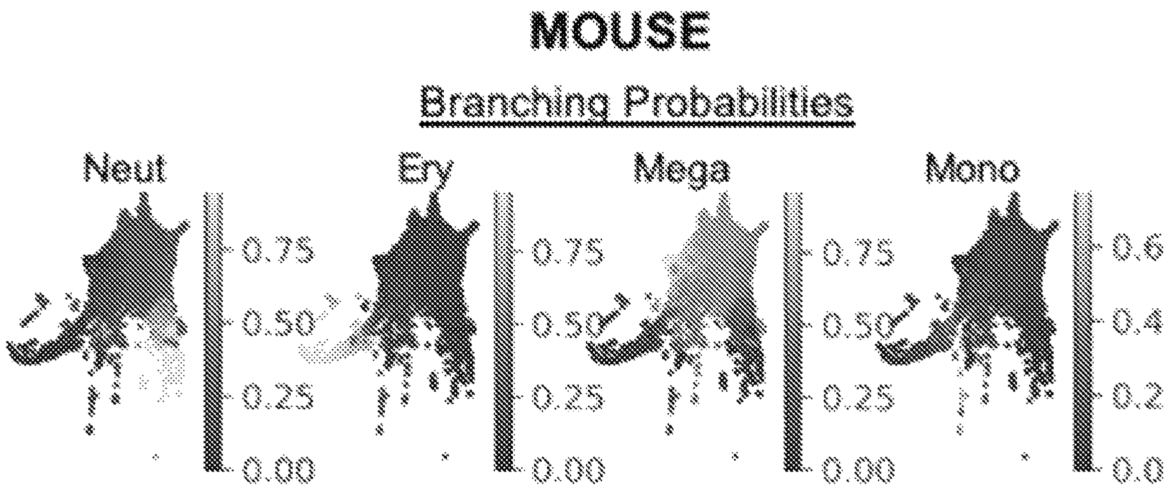
FIG. 12C shows murine individual branching probabilities.
Figure 12D:
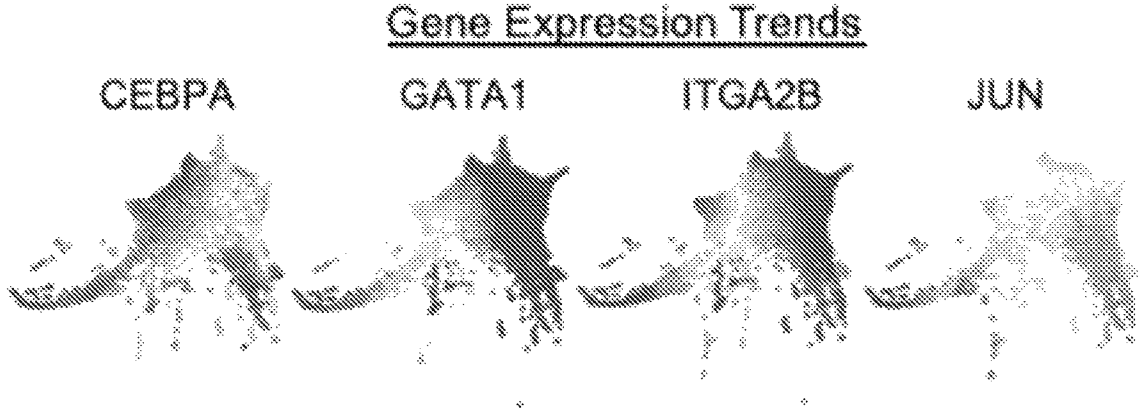
FIG. 12D shows additional murine gene expression trends.
Figure 12E:
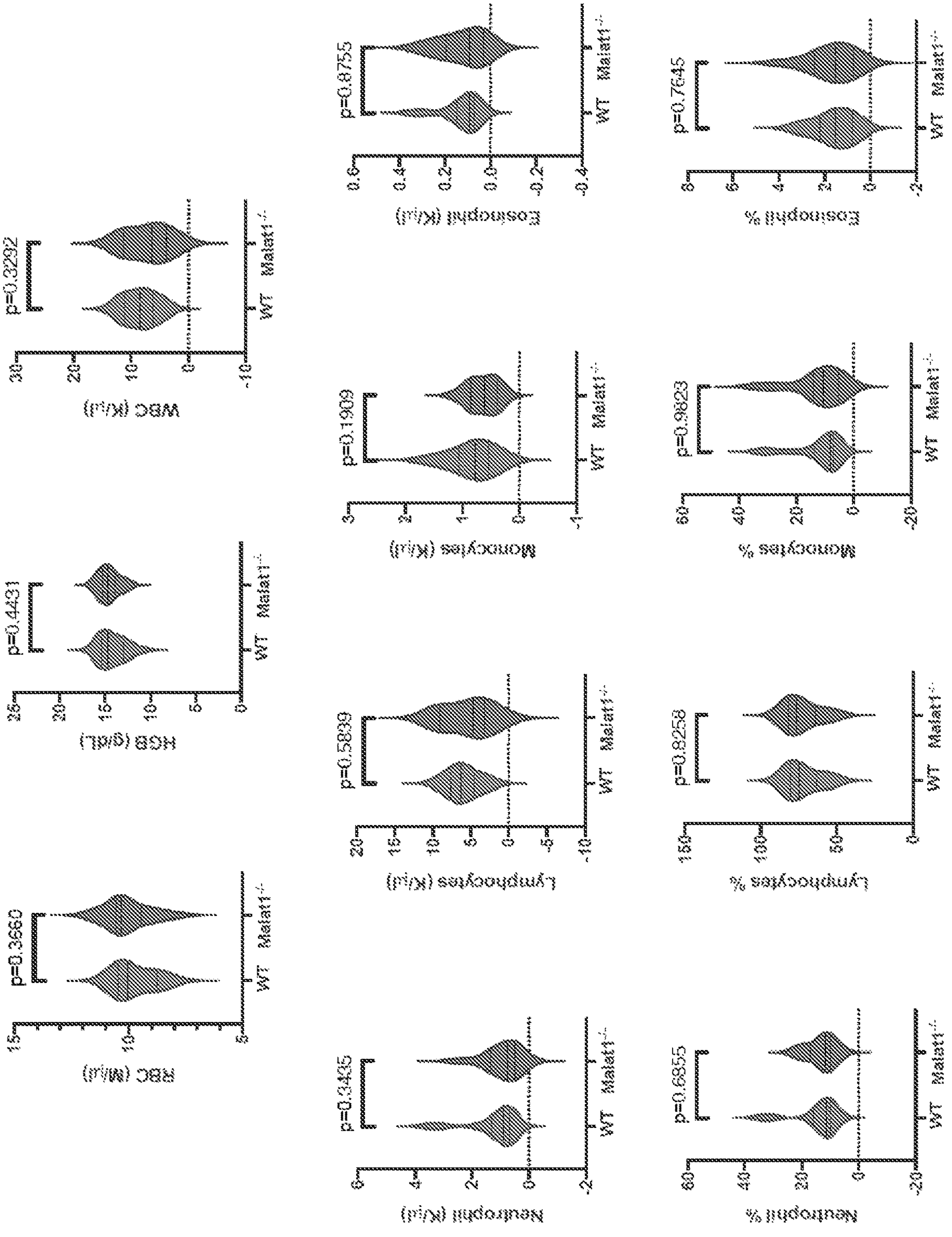
FIG. 12E shows CBC analysis from C57BL/6 vs MALAT1$^{-/-}$ mice.

To explore the functional relevance of MALAT1 in HSC the hematopoietic compartment of transgenic MALAT1 KO mice was immunophenotypically evaluated. HSPCs and their subsets HSC, MPP1, MPP2, MPP3, and MPP4 were identified as previously described (Wilson, A. et al. Cell 2008 135:1118-1129). While no differences in LSK or MPP populations were observed, statistically significant lower HSC numbers were identified in MALAT1 KO mice compared to controls (FIG. 6I). Complete blood counts revealed no difference between MALAT1 KO and controls (FIG. 12E). To evaluate the self-renewal capacity of MALAT1 KO cells, an admixture of CD45.2 MALAT1 KO BMNCs and CD45.1 wild type BMNCs were transplanted into lethally irradiated congenic recipients at a ratio 1:1. Peripheral blood chimerisms did not change over 20 weeks suggesting that there are were no differences in self renewal capacity when comparting MALAT1 KO and wild type BMNCs (FIG. 6J). Collectively, this data suggests that MALAT1 is expressed highly in HSC and is necessary for normal number of HSC but does not impact self-renewal capacity.

MALAT1 depletion results in myelomonocytic differentiation in murine and human models of CMML.

Figure 7A:
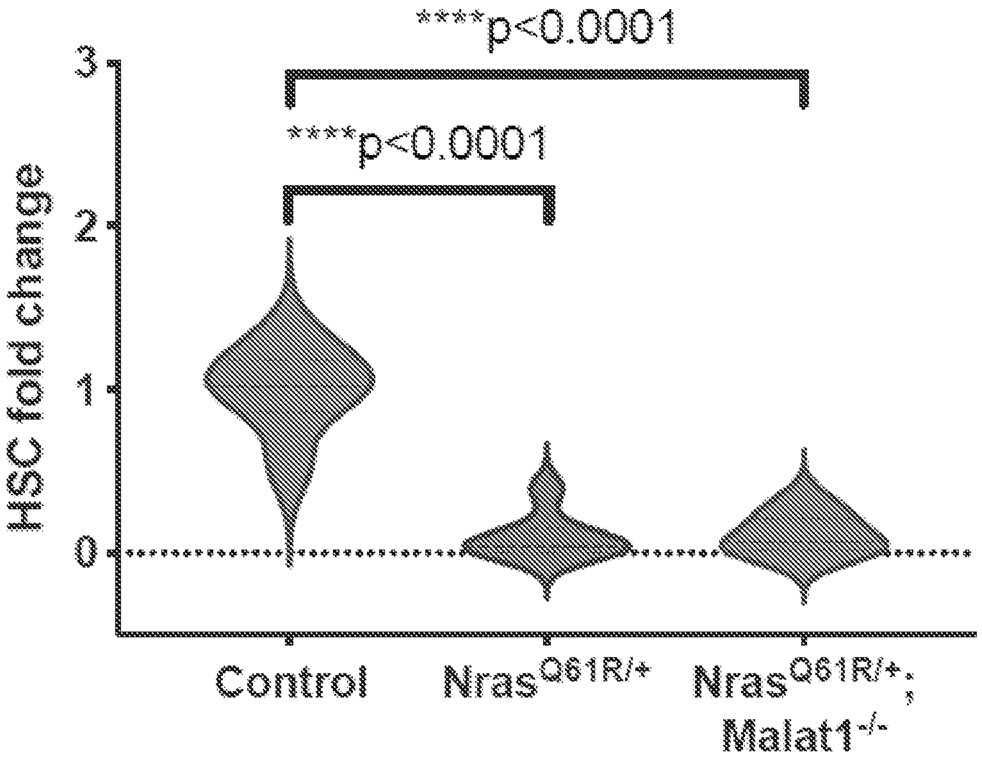
FIGS. 7A to 7F show MALAT1 depletion results in myelomonocytic differentiation in murine and human models of CMML.
Figure 7B:
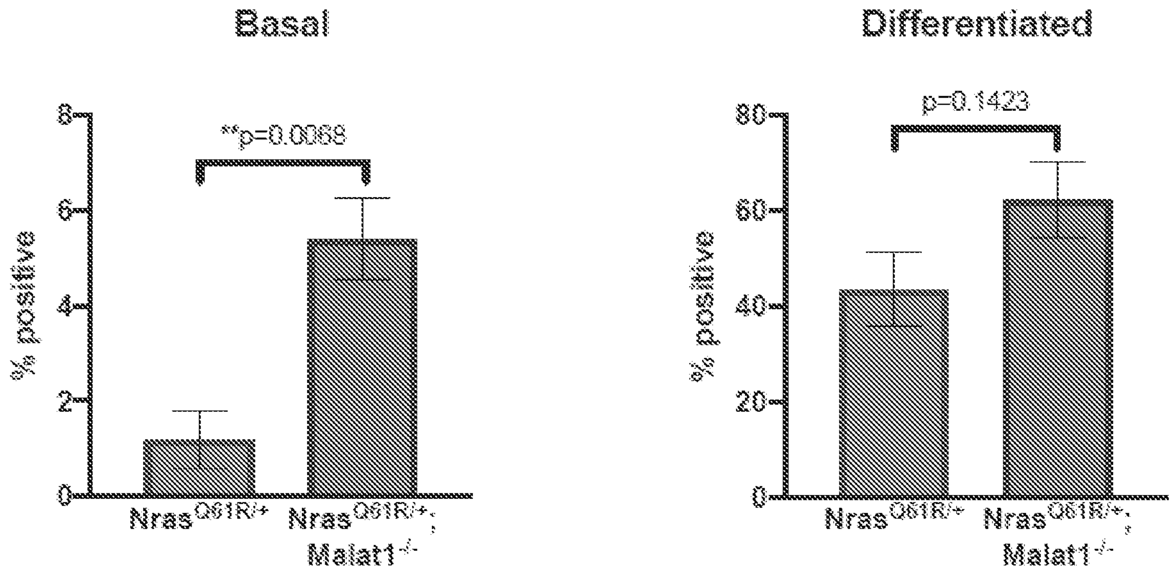
Figure 13A:
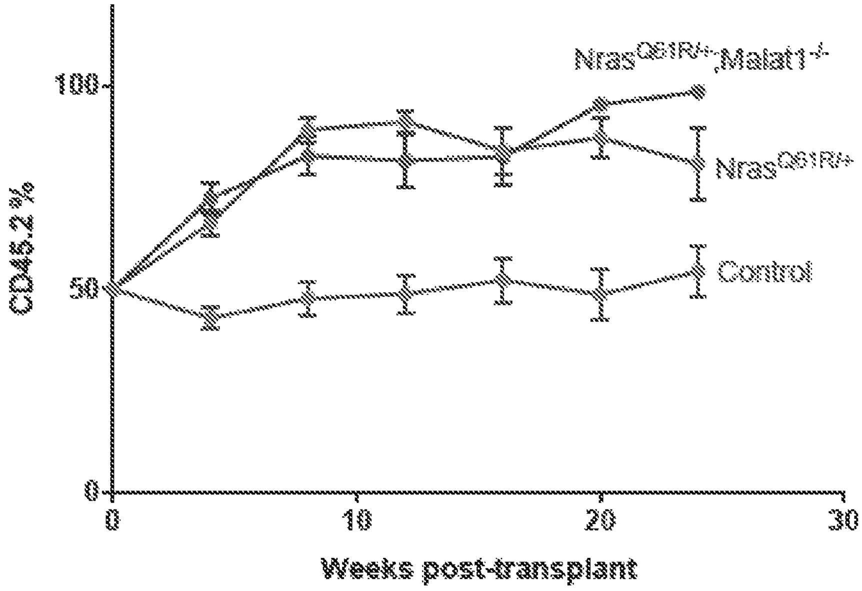
FIG. 13A shows competitive transplant: Nras$^{Q61R/+}$ vs Nras$^{Q61R/+}$ Malat1$^{-/-}$ BM.
Figure 13B:
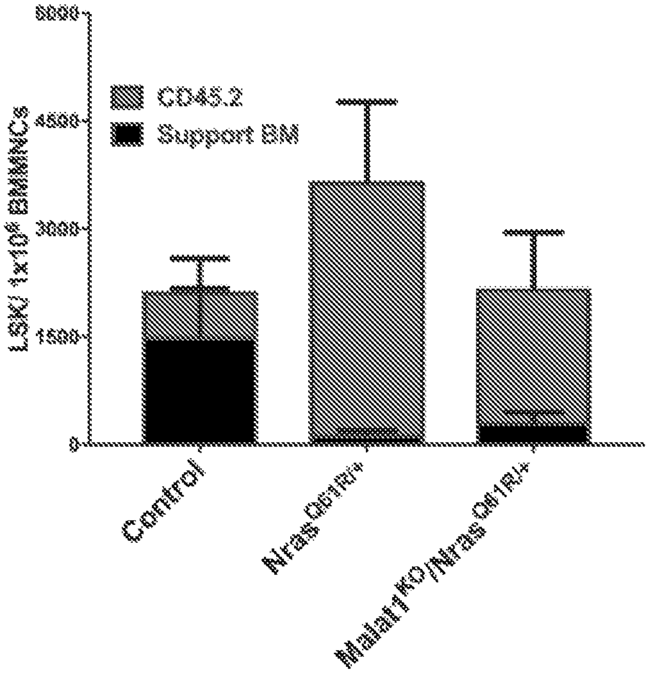
FIG. 13B shows LSK proportions in Mx1-Cre vs Nras$^{Q61R/+}$ vs Nras$^{Q61R/+}$ Malat1$^{-/-}$.
Figure 13C:
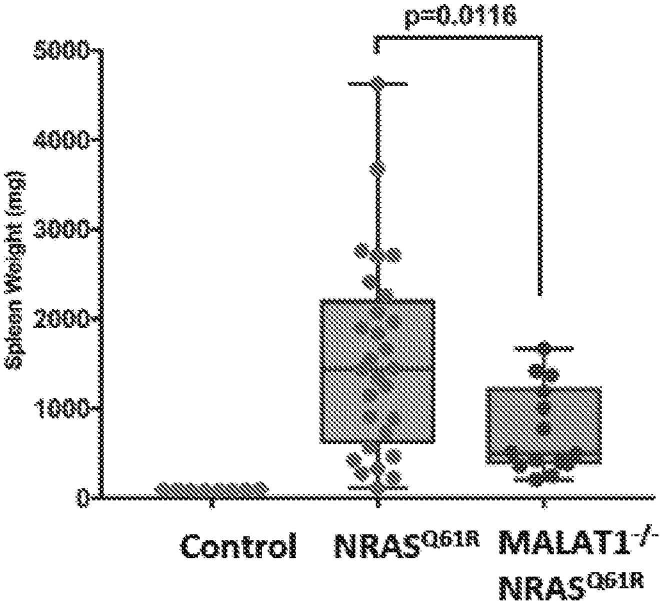
FIG. 13C shows spleen weights in Mx1-Cre vs Nras$^{Q61R/+}$ vs Nras$^{Q61R/+}$ Malat1$^{-/-}$.
Figure 13D:
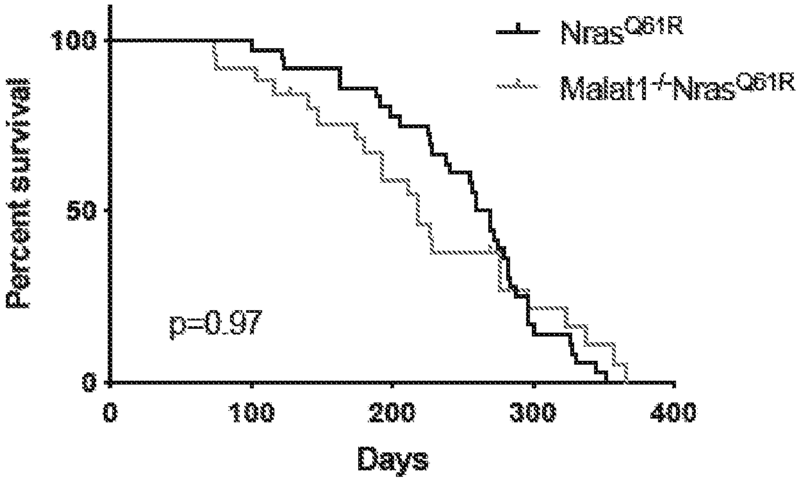
FIG. 13D shows survival in Nras$^{Q61R/+}$ vs Nras$^{Q61R/+}$ Malat1$^{-/-}$.
Figure 13E:
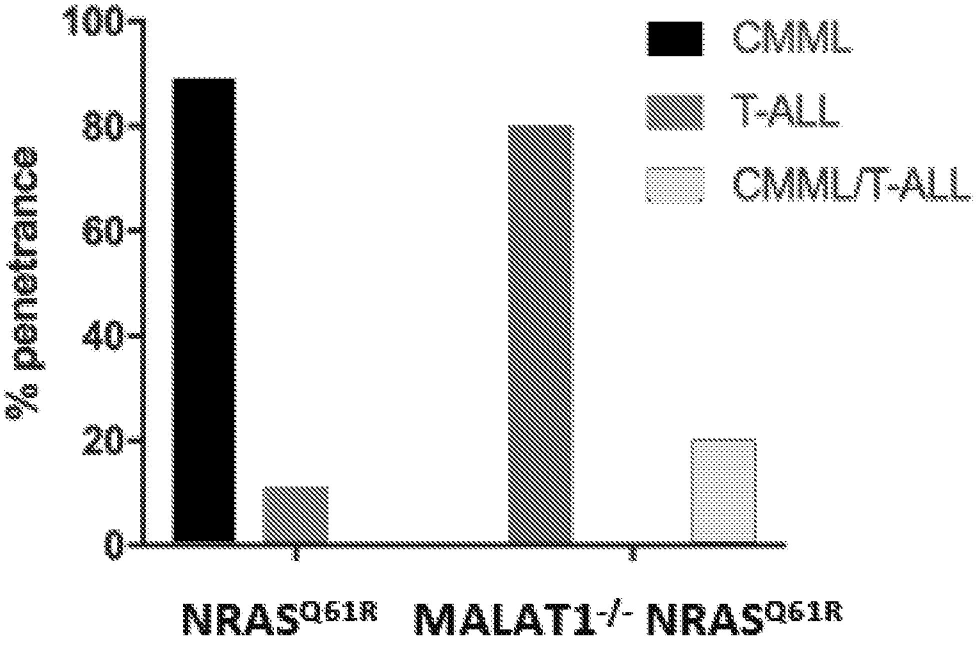
FIG. 13E shows disease penetrance in Nras$^{Q61R/+}$ vs Nras$^{Q61R/+}$ Malat1$^{-/-}$.
Figure 14A:
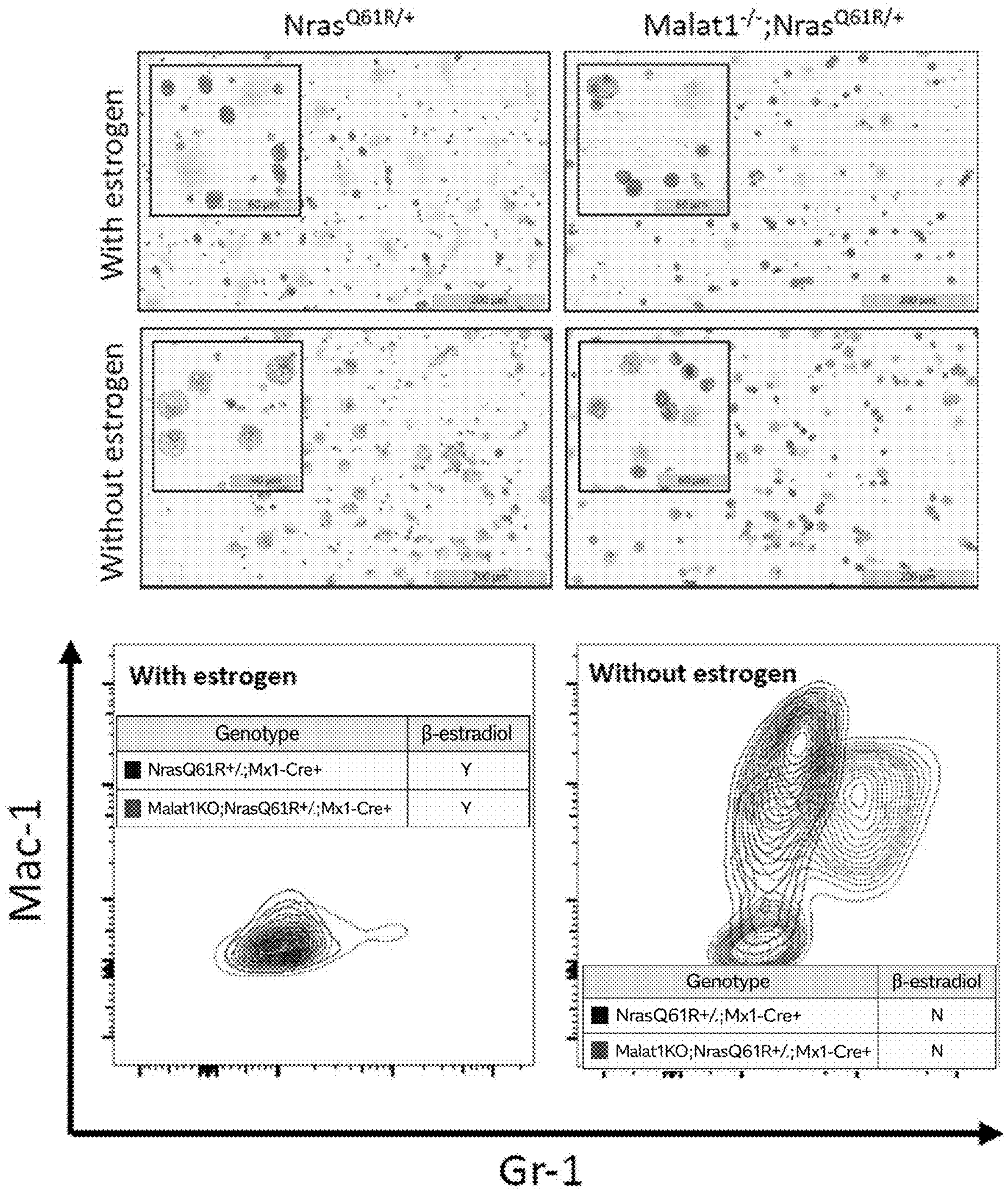
FIG. 14A shows immortalized murine Nras$^{Q61R/+}$and Nras$^{Q61R/+}$Malat1$^{-/-}$ cells: i) May-Grunwald-Giemsa staining, and ii) basal and differentiated Mac-1 and Gr-1 staining.
Figure 14B:
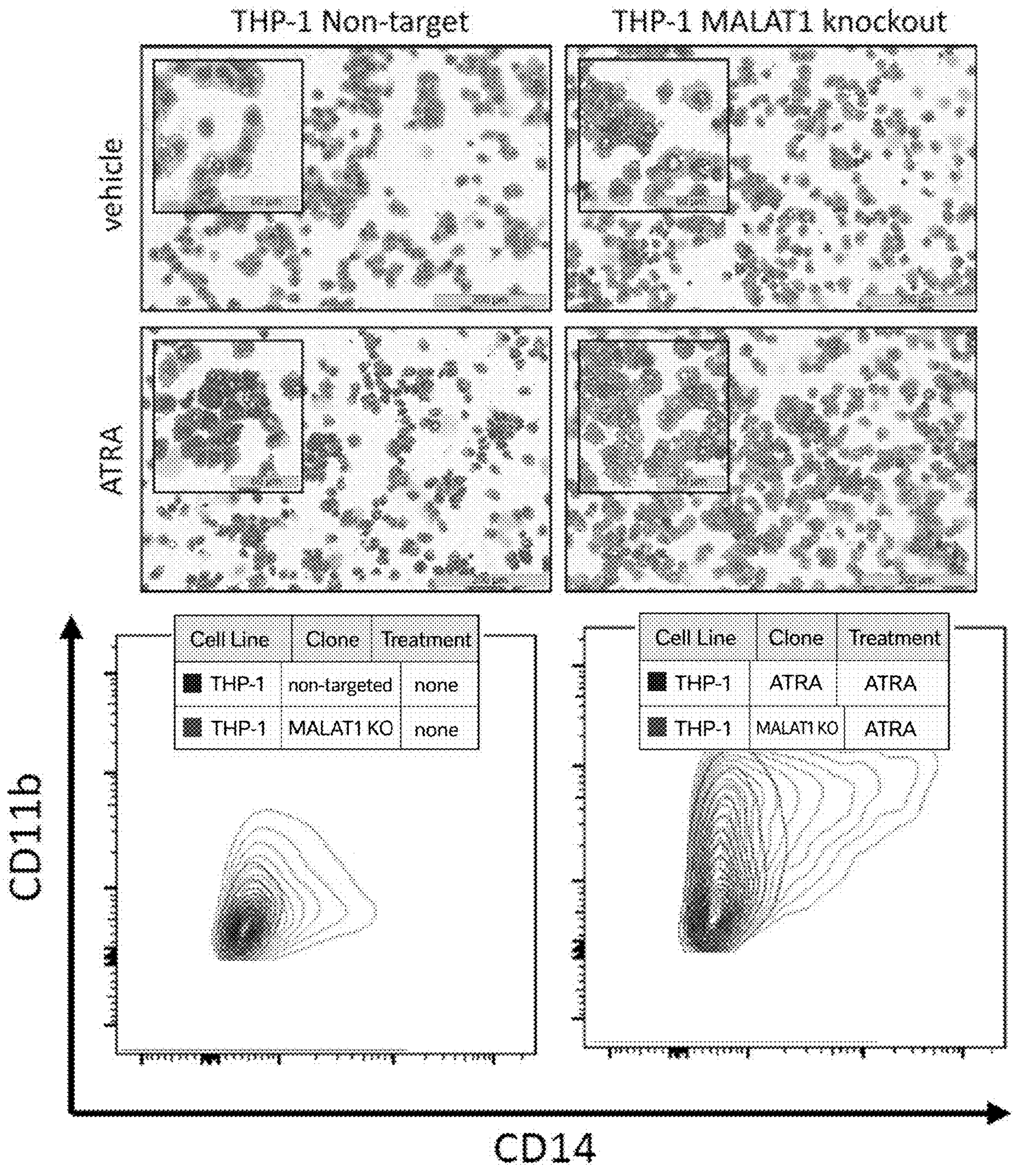
FIG. 14B shows THP-1 MALAT1 WT and CRISPR KO cells: i) May-Grunwald-Giemsa staining, and ii) basal and differentiated Mac-1 and Gr-1 staining.
Figure 14C:
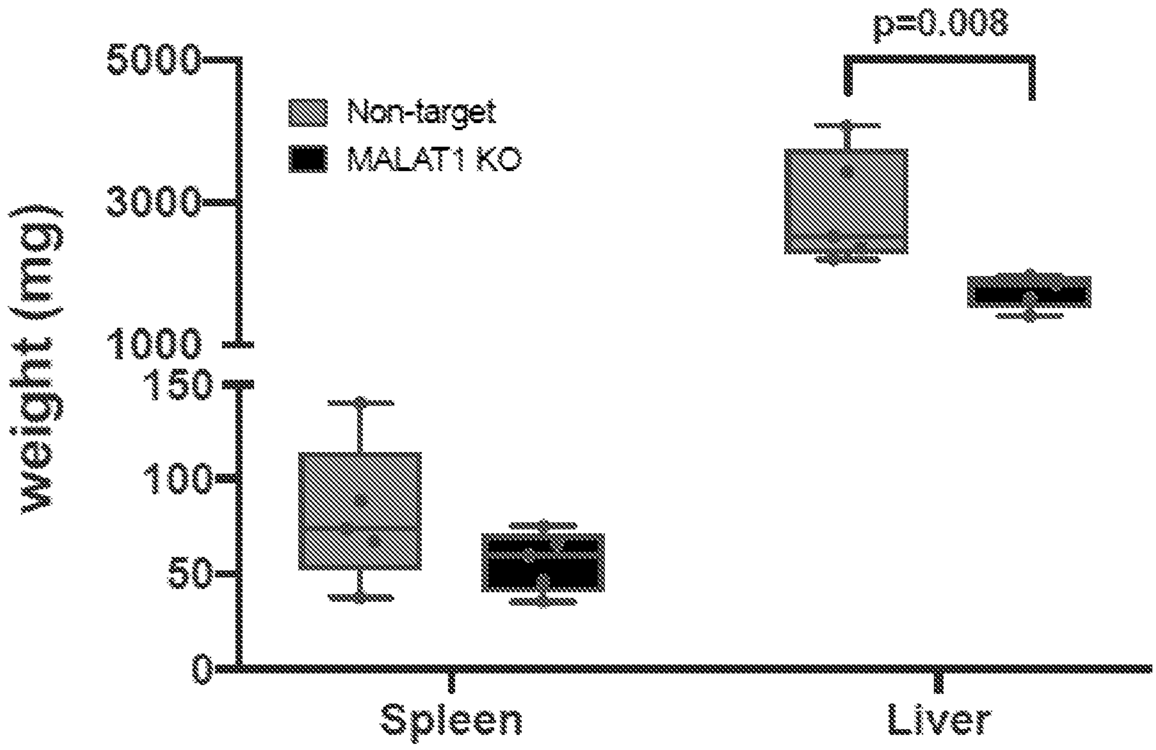
FIG. 14C shows spleen and liver weights from THP-1 xenografts.
Figure 14D:
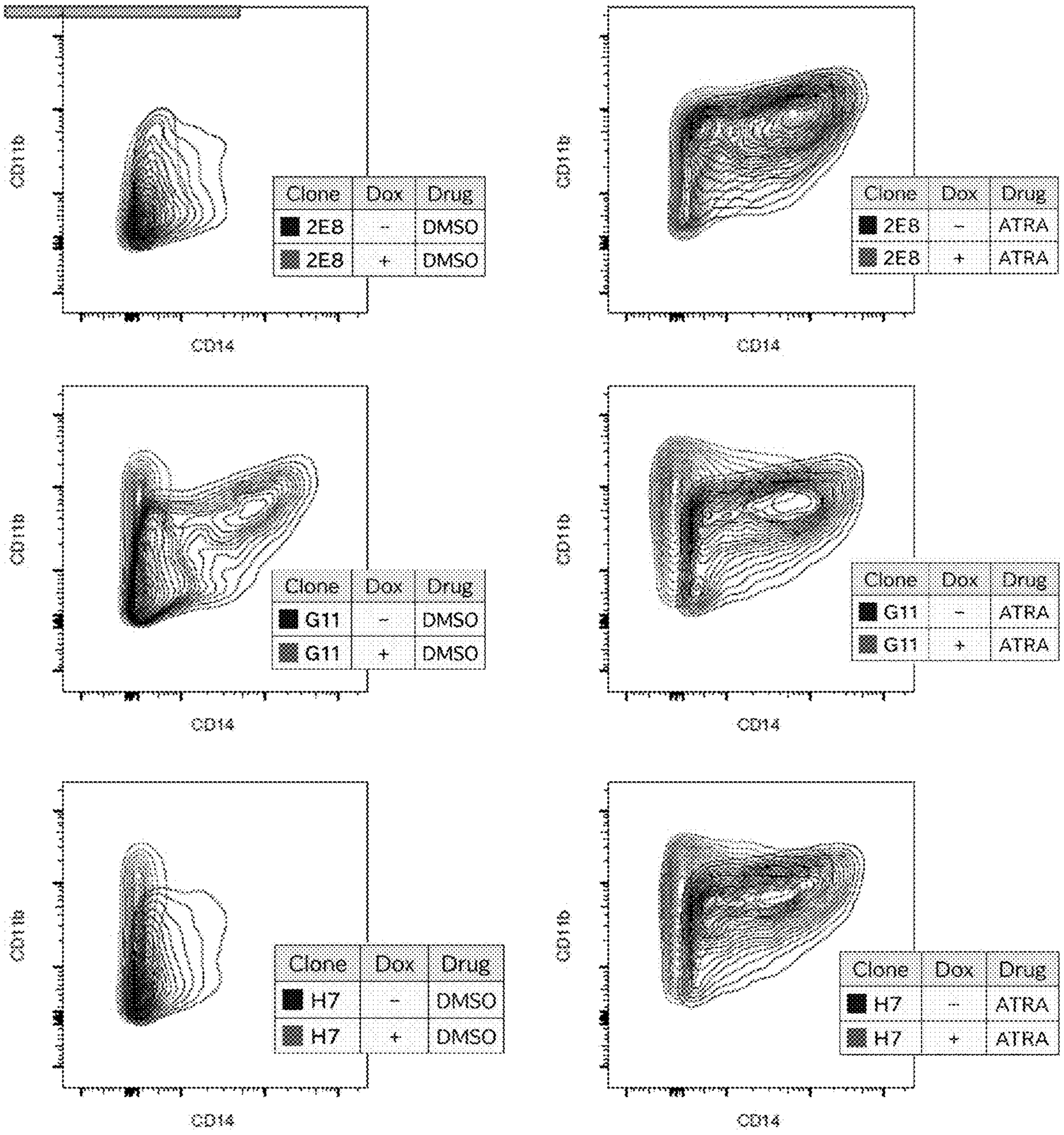
FIG. 14D shows flow plots from THP-1 rescue experiment

Given that MALAT1 expression is elevated and clinically and functionally relevant in CMML and HSCs respectively, the effect of MALAT1 depletion on myeloid differentiation was explored in models of CMML. To model CMML, the floxed NRAS$^{Q61R/+}$ mouse was used because it displays a CMML-like phenotype and is a heterozygous genetic model similar to that seen in human CMML (Kong, G. et al. Leukemia 2016 30:1935). NRAS$^{Q61R/+}$/MALAT1$^{KO/KO}$ mice driven by Mx1-Cre were then generated. After plpC injection of both NRAS$^{Q61R/+}$ and NRAS$^{Q61R/+}$/MALAT1$^{KO/KO}$ mice, the characteristic CMML phenotype was observed by 10 weeks in the peripheral blood of both models. Additionally, a statistically significant decrease in spleen weight when compared to NRAS$^{Q61R/+}$was observed without measurable differences in survival or penetrance (FIG. 13A-C). Next, BMNCs were harvested from each model and transformed BMNCs with an estrogen-regulated Hoxb8 (ER-Hoxb8) construct as previously described (Wang, G. G. et al. Nat Methods 2006 3:287-93). These transformed cells can be cultured and remain in a hematopoietic stem and progenitor cell (HPSC) state in vitro until estradiol is withdrawn from the culture media and myeloid differentiation is induced. Using these transformed cells, it was possible to recapitulate the expected differentiation seen upon estradiol withdrawal in wild type cells as measured by CD11b and CD14 expression. Importantly, there was both an increase in basal expression of differentiation markers and an even larger increase in CD11b and CD14 positive cells upon estradiol withdrawal in MALAT1 depleted cells, suggesting that MALAT1 depletion can promote myelomonocytic differentiation (FIG. 7A). HSC numbers were slightly decreased in the NRAS$^{Q61R/+}$/MALAT1$^{KO/KO}$ mice compared to controls, and self-renewal capacity was unaffected as measured by in vivo competitive transplants consistent with results seen in non-leukemic transgenic models (FIGS. 7B, 13D-E).

Figure 7C:
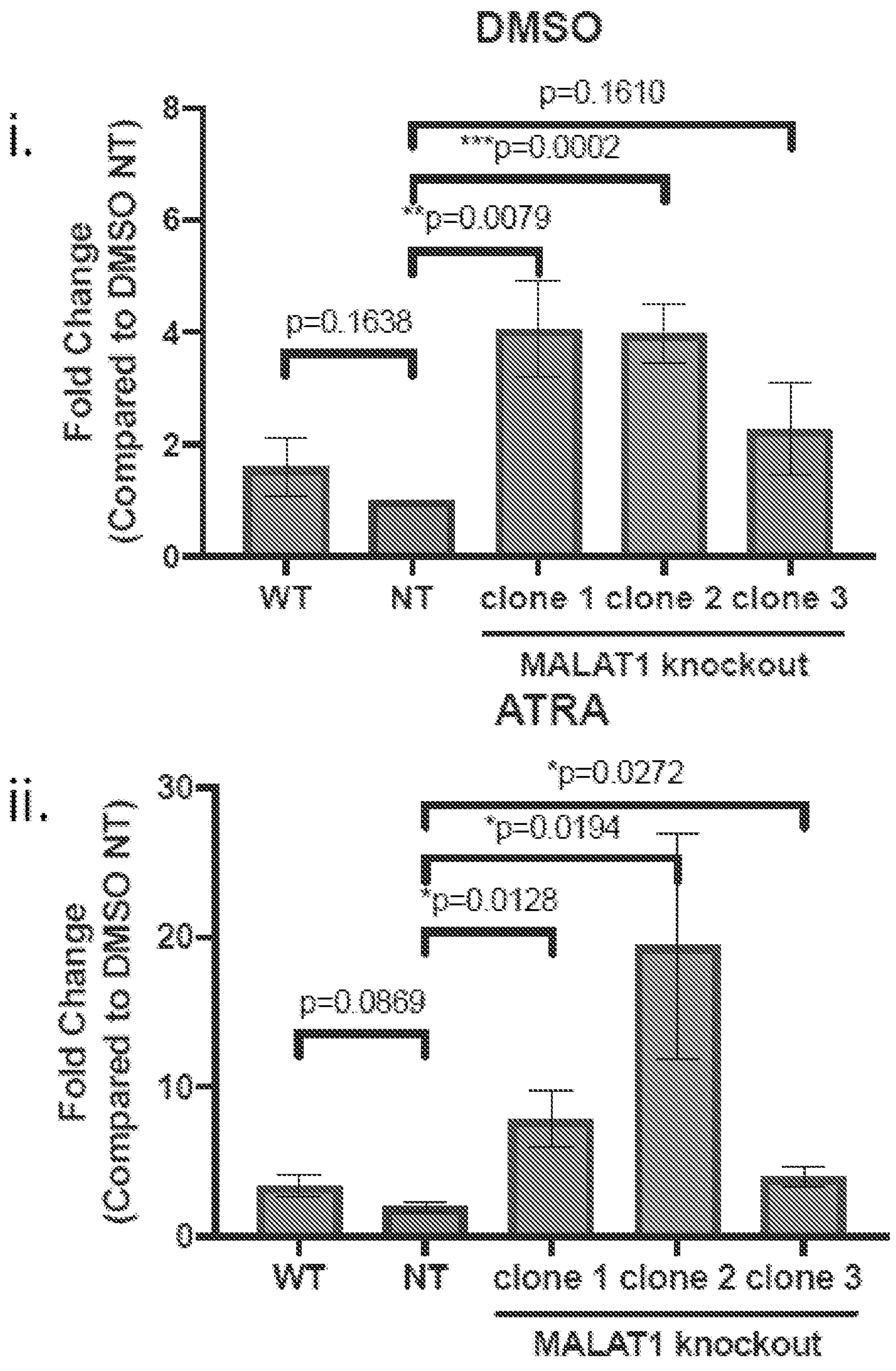
Figure 7D:
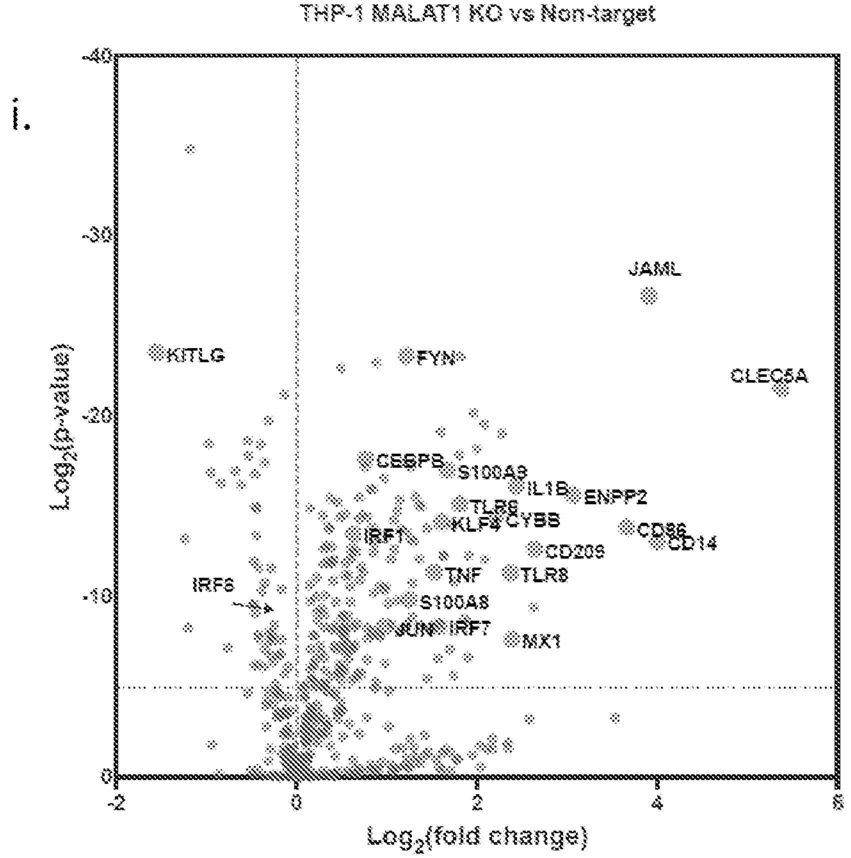
Figure 7D:
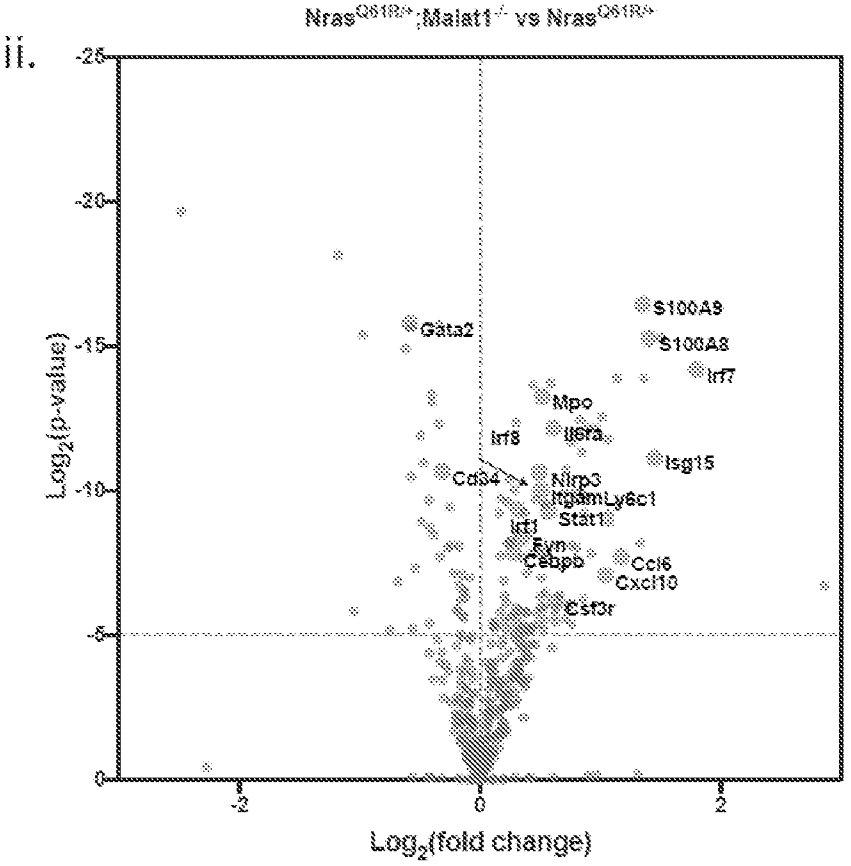
Figure 7E:
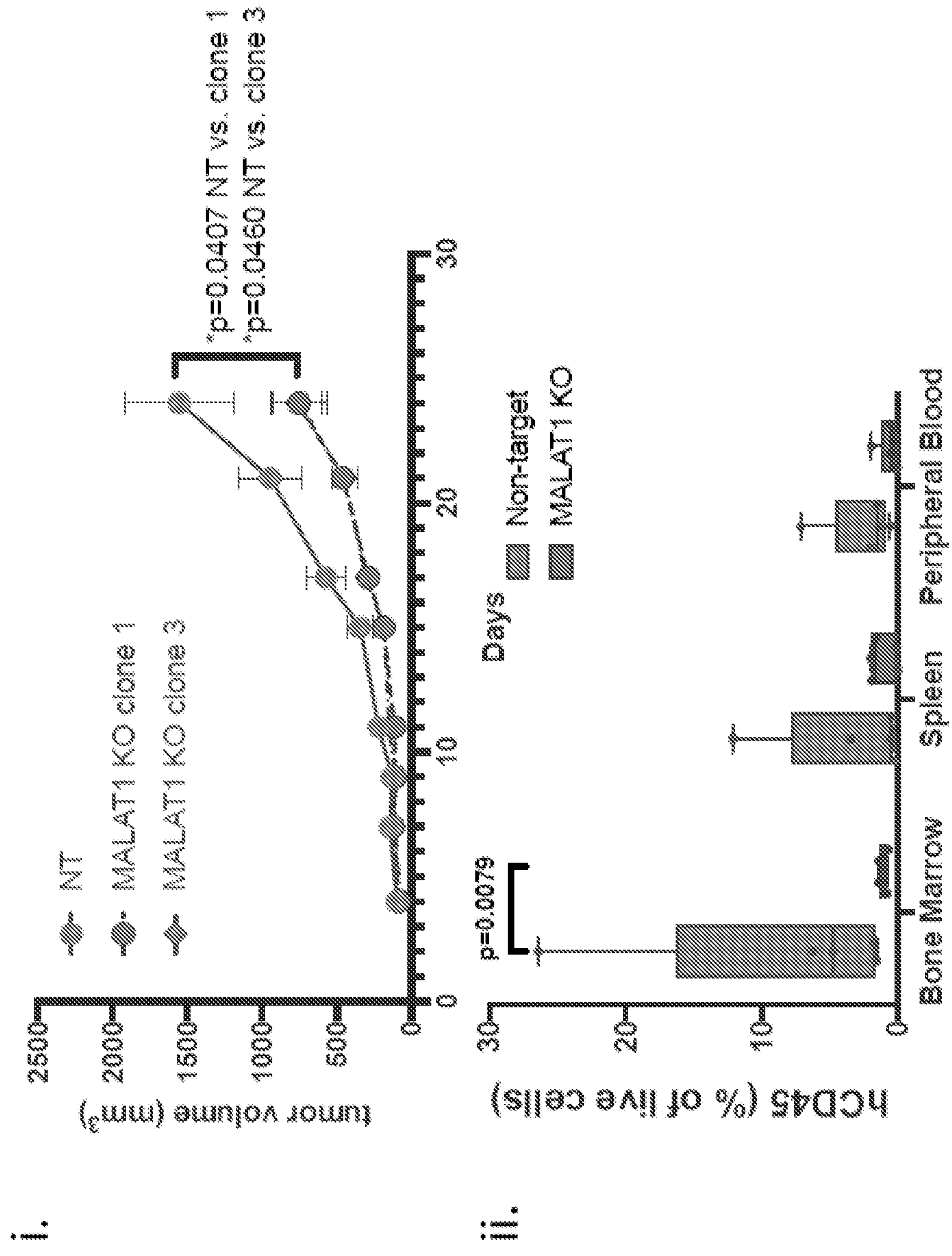

To confirm that MALAT1 depletion could induce differentiation in human models of leukemia, MALAT1's major transcriptional start site was deleted via CRISPR/Cas9 as previously described in several single cell derived clones of the THP-1 cell line. THP-1 cells were chosen because they were derived from a patient with acute monocytic leukemia, they harbor an NRAS mutation, and they had the highest levels of MALAT1 in our screen of myeloid cell lines. As observed in murine models of CMML, MALAT1 depletion resulted in basal increases in differentiation markers and a more robust response to both PMA and All-trans Retinoic Acid (ATRA) suggesting that the differentiation phenotype is preserved between mouse and human (FIG. 7C). These findings were orthogonally validated in mouse and human by examining morphologic and transcriptional analysis in MALAT1 depleted versus controls cells which demonstrated a decreased nucleus to cytoplasm ratio, increased vacuolization and upregulation of markers of terminal myelomonocytic differentiation, respectively (FIGS. 7D, 13F-G). Moreover, heterotopic and orthotopic xenografts of MALAT1 deleted THP-1 cells demonstrated decrease tumor volume and leukemic engraftment, respectively (FIG. 7E)

Figure 7F:
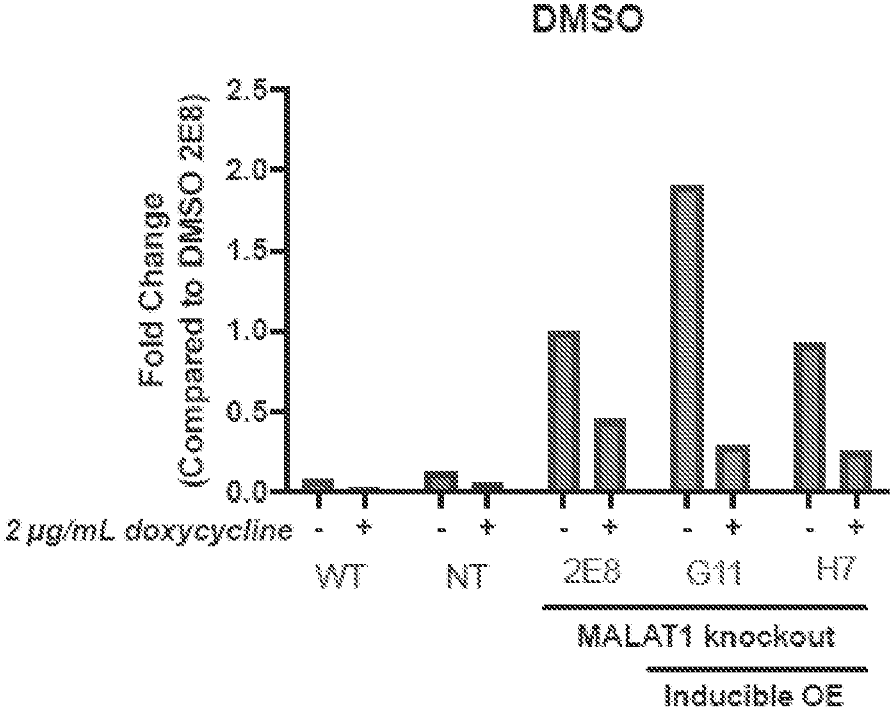
Figure 7F:
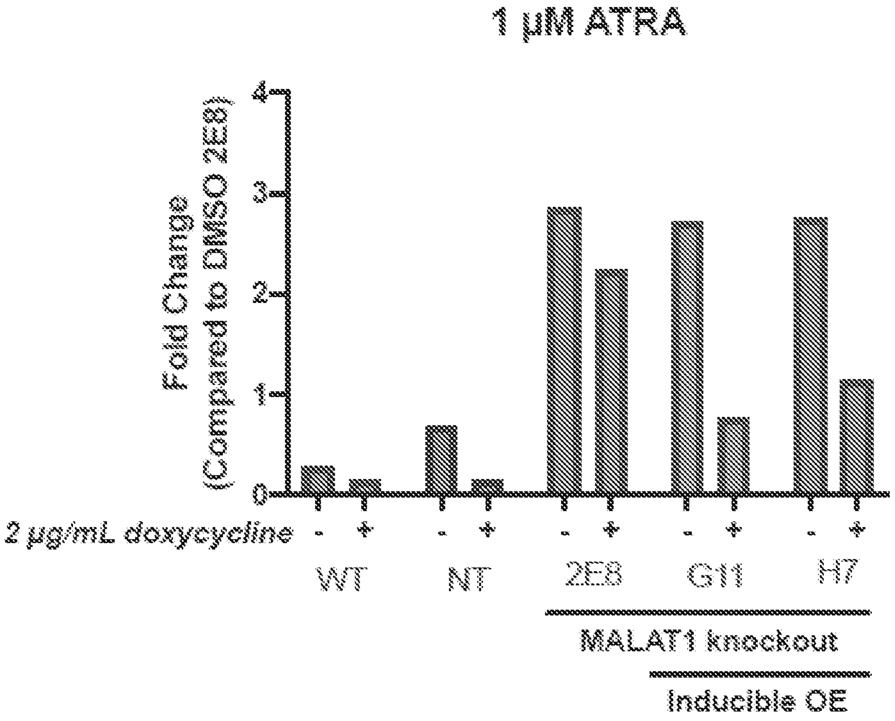

Several recent reports suggest that the phenotype of lncRNAs, and MALAT1 specifically, have been observed because of the on-target deletion of cis regulatory elements controlling neighboring coding genes rather than the lncRNAs itself. To ensure that this was not the case in our system, MALAT1 was overexpressed in THP-1 MALAT1 deleted cells restoring normal differentiation in the context of both PMA and ATRA treatment, suggesting that the observed phenotype is MALAT1 specific (FIG. 7F).

Figure 8A:
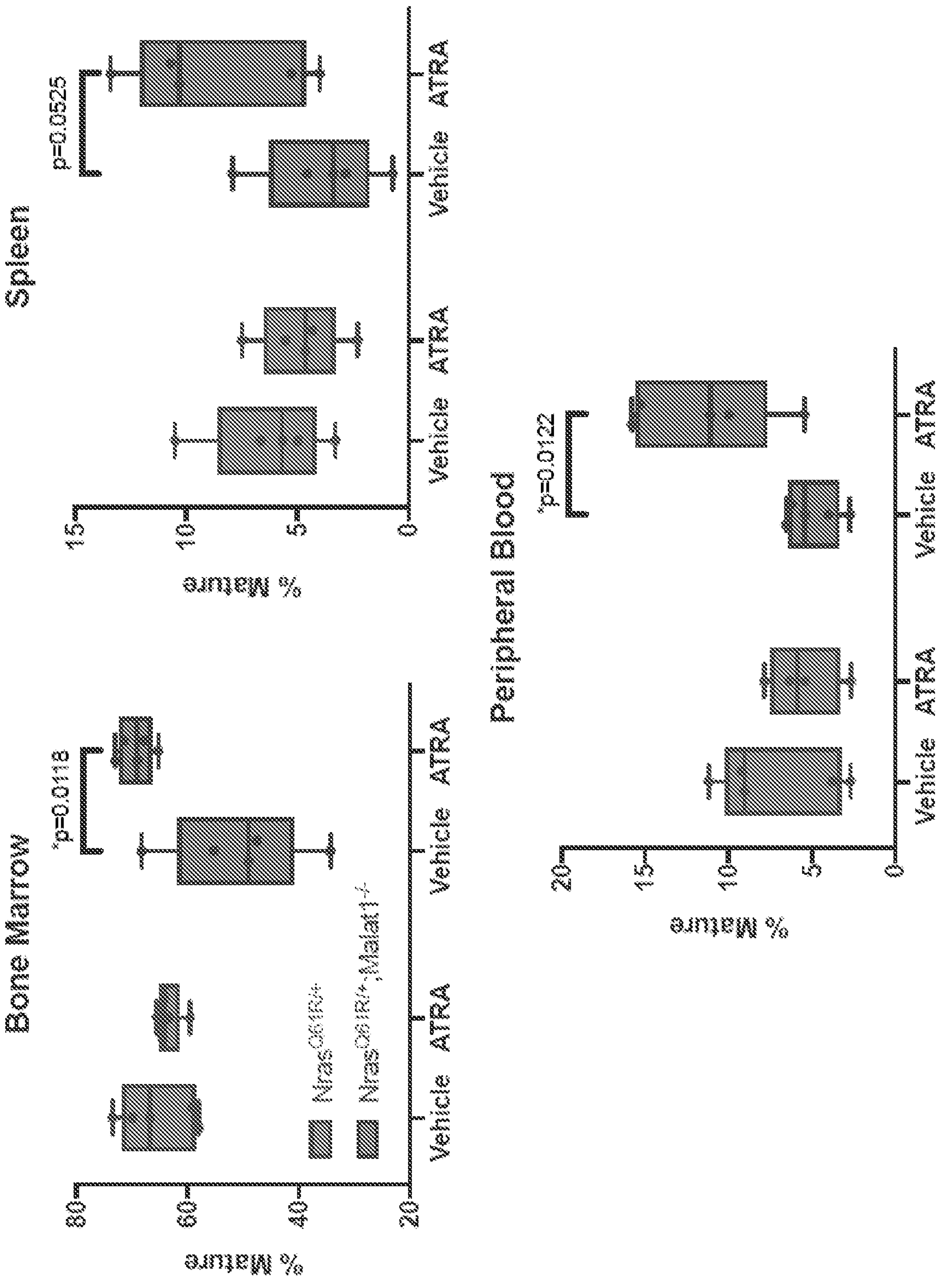
FIGS. 8A to 8C show in vivo differentiation therapy in GEMM model of CMML.
Figure 8B:
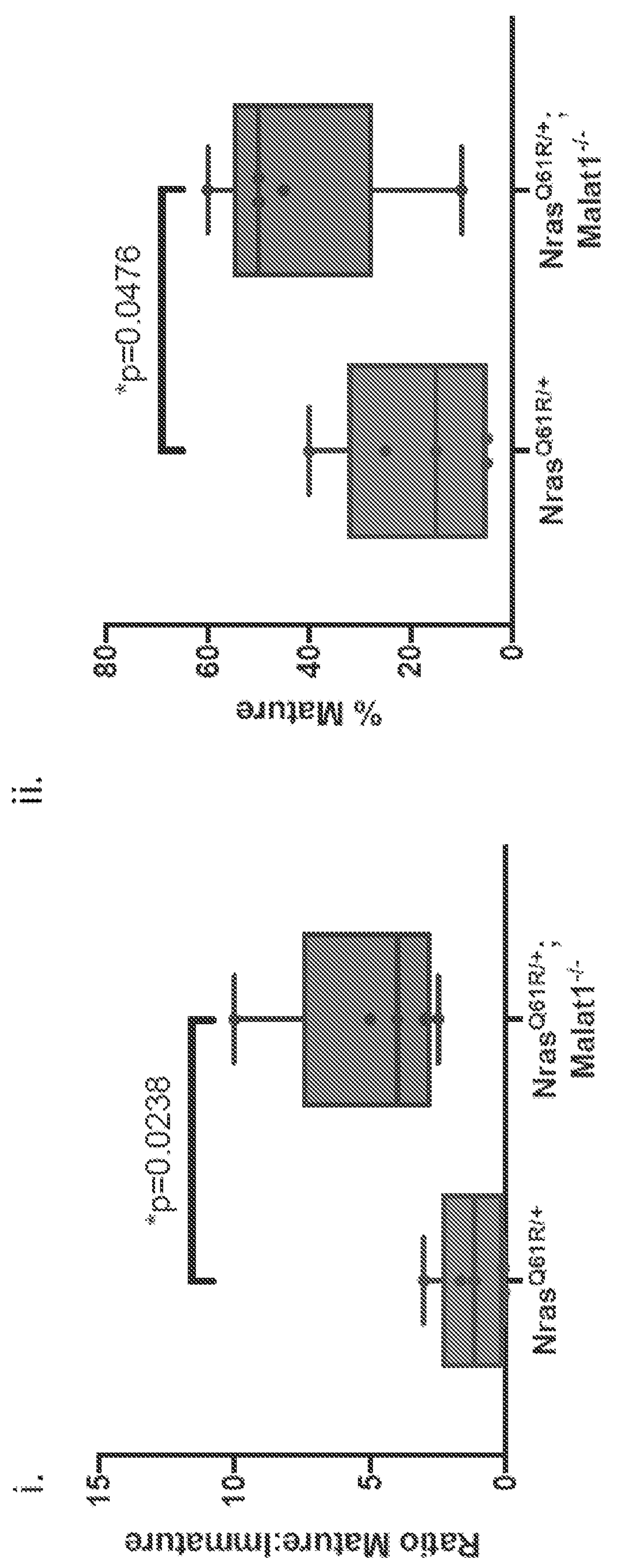
Figure 8C:
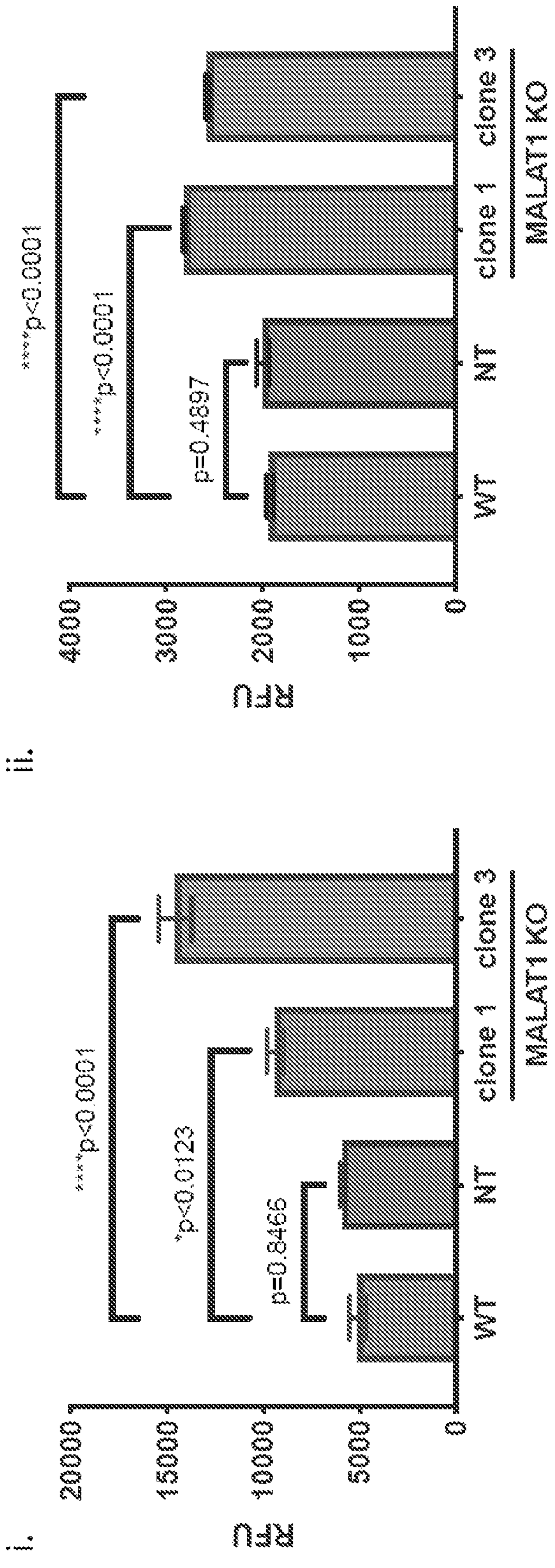

To validate the differentiation effect in vivo primary transplants were generated from NRAS$^{Q61R/+}$/MALAT1$^{KO/KO}$ and NRAS$^{Q61R/+}$ followed by treatment with ATRA. Although no basal differences in differentiation were observed, statistically significant differences in differentiation markers were identified when mice were treated with ATRA intraperitoneally in NRAS$^{Q61R/+}$/MALAT1$^{KO/KO}$ mice but not controls (FIG. 8A). As has been clinically observed in ATRA treated acute promyelocytic leukemia (APL) patients, NRAS$^{Q61R/+}$/MALAT1$^{KO/KO}$ mice displayed in vivo and in vitro evidence of differentiation syndrome. Differentiation syndrome is a treatable but potentially fatal complication of approved therapies which induce differentiation in myeloid neoplasms hallmarked by increases in myeloid cell adhesion, invasion, and ultimately lung infiltration. There was a higher proportion of terminally differentiated cells in the lungs of NRAS$^{Q61R/+}$/MALAT1$^{KO/KO}$ mice compared to controls (FIG. 8B). Further, MALAT1 depleted THP-1 cells had increased adhesion and endothelial migration compared to controls consist with an increased potential for differentiation syndrome (FIG. 8C).

MALAT1 depletion in combination with ATRA impairs engraftment in patient derived xenograft (PDX) models of CMML.

Figure 9A:
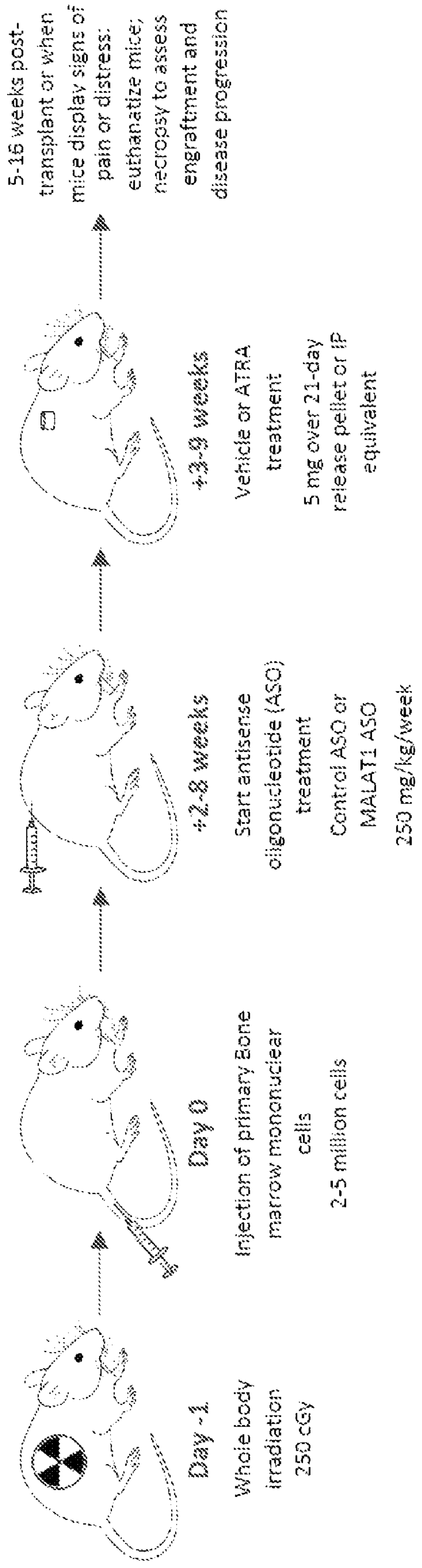
FIGS. 9A to 9C show MALAT1 depletion in combination with ATRA impairs engraftment in PDX models of CMML.
Figure 9B:
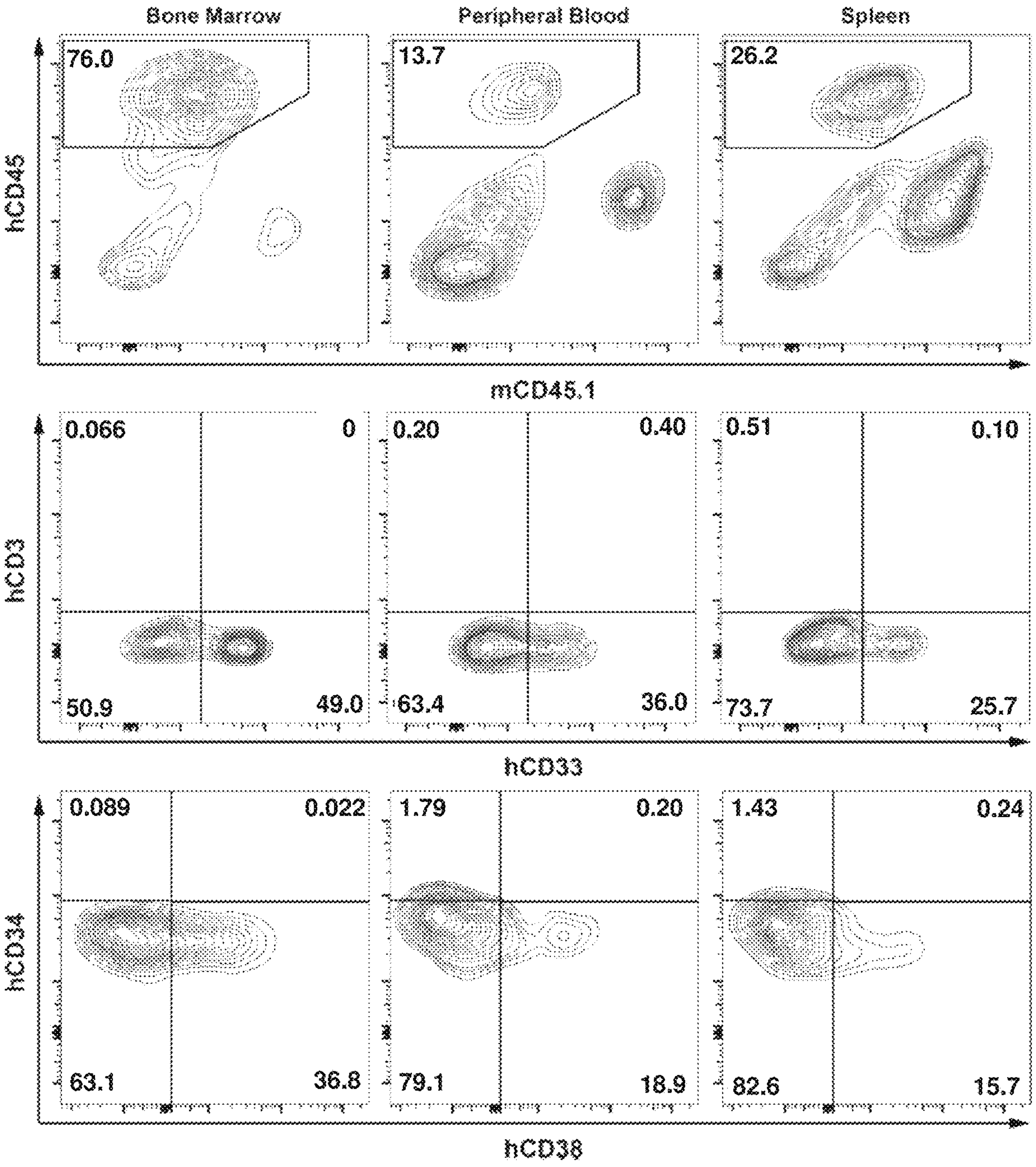
Figure 9C:
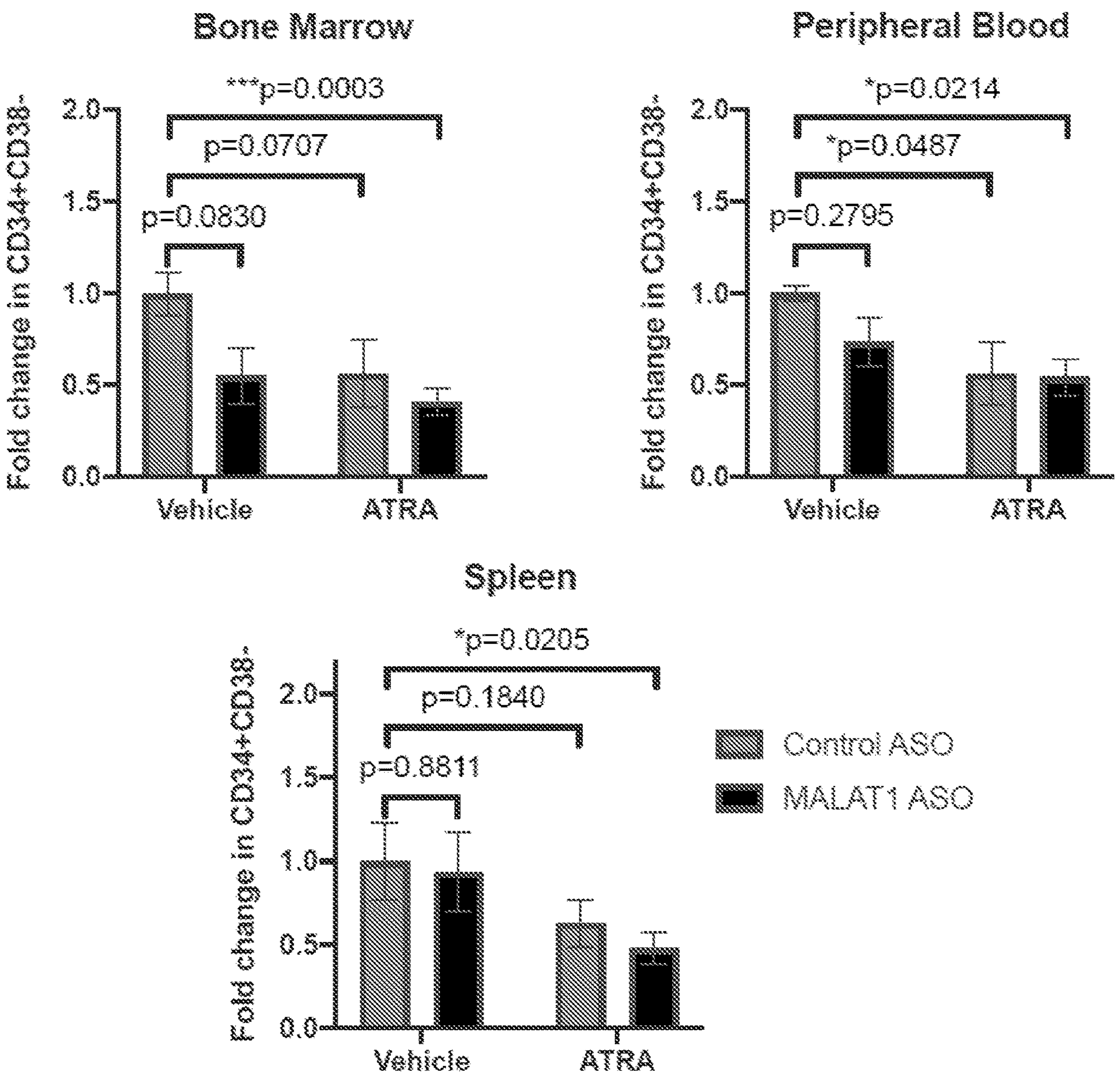

The therapeutic potential of MALAT1 and ATRA therapy in primary CMML samples was next investigated. To deplete MALAT1 in this context, antisense olignonucleotides (ASOs) were used that are currently in clinical development that profoundly deplete MALAT1 in human monocytic leukemia cells and have been evaluated in preclinical models of breast cancer. To test their efficacy with or without ATRA in primary samples, CMML PDX models were generated by transplanting 2 million bone marrow mononuclear cells into NSG-S mice as previously described. These models accurately recapitulate the clinical, pathologic, and genetic aspects of the human condition making them ideal models to credential this therapeutic approach. Models were generated, after two weeks, were treated with either vehicle and control ASO, ATRA and control ASO, vehicle and MALAT1 ASO, or ATRA and MALAT1 ASO. All PDX models were then sacrificed and human engraftment and differentiation were evaluated by flow cytometry. Using this approach, a decrease was observed in Lin-CD34+ CD38+ human cells in MALAT1 ASO treated alone and in combination with ATRA across bone marrow peripheral blood and spleen (FIG. 9A-9C).

Overexpression of the transcription factor CREB is sufficient to reverse the differentiation induced by MALAT1 depletion.

Figure 10A:
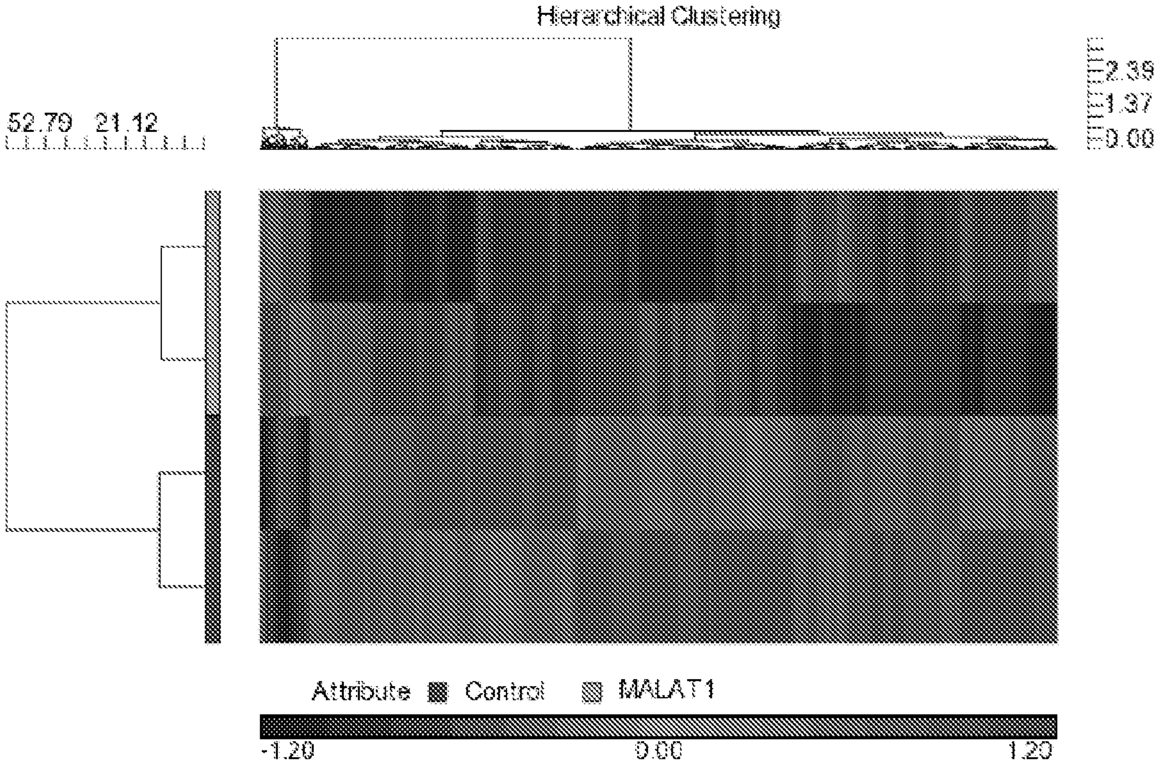
FIGS. 10A to 10G show overexpression of the transcription factor CREB is sufficient to reverse the differentiation induced by MALAT1 depletion.
Figure 10B:
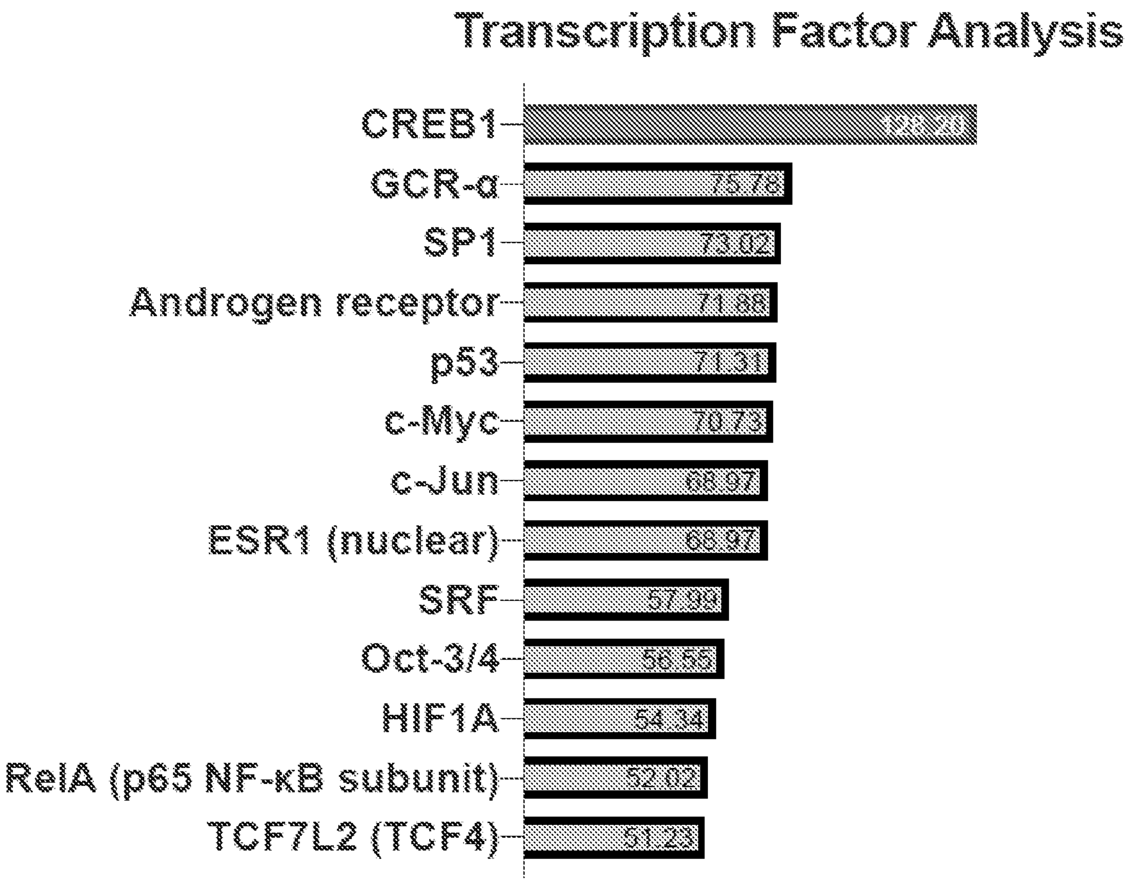
Figure 10C:
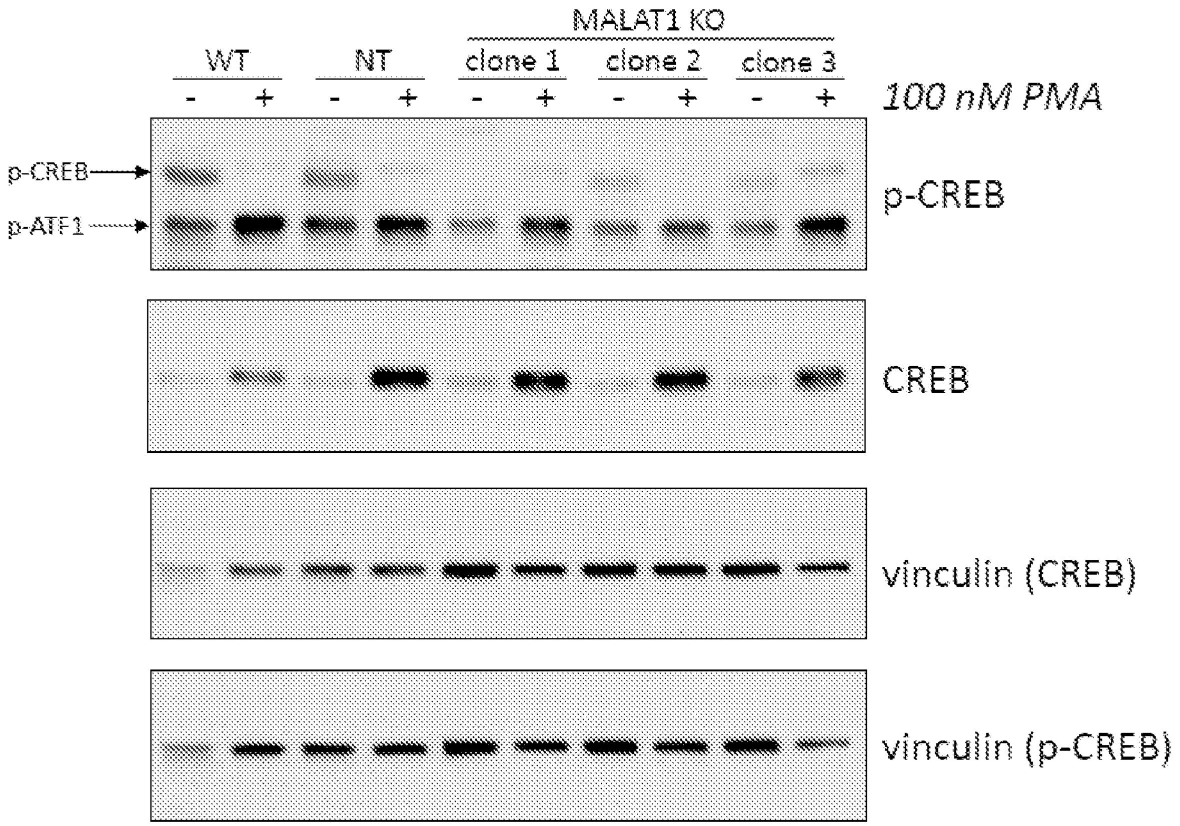
Figure 10D:
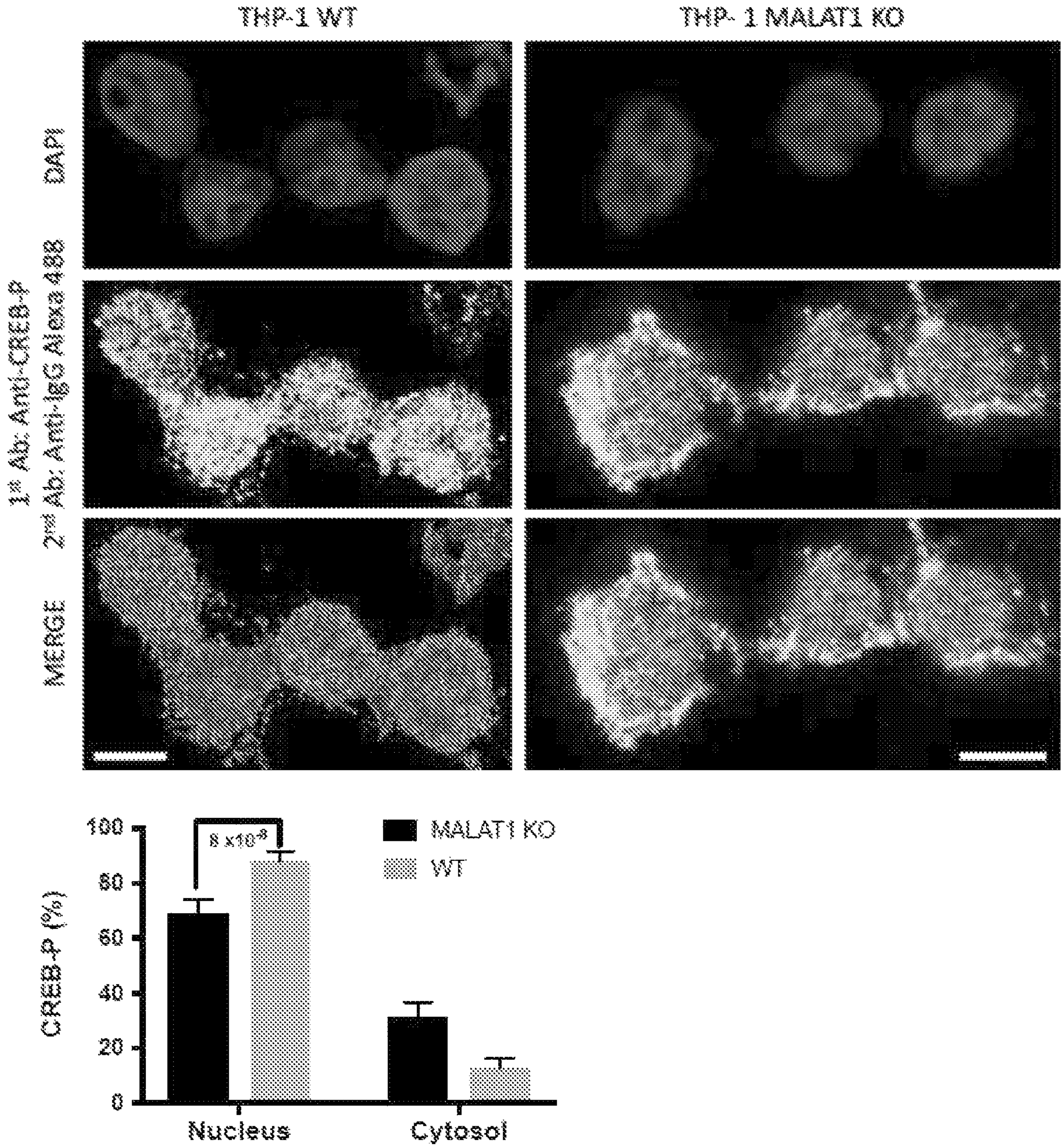
Figure 10E:
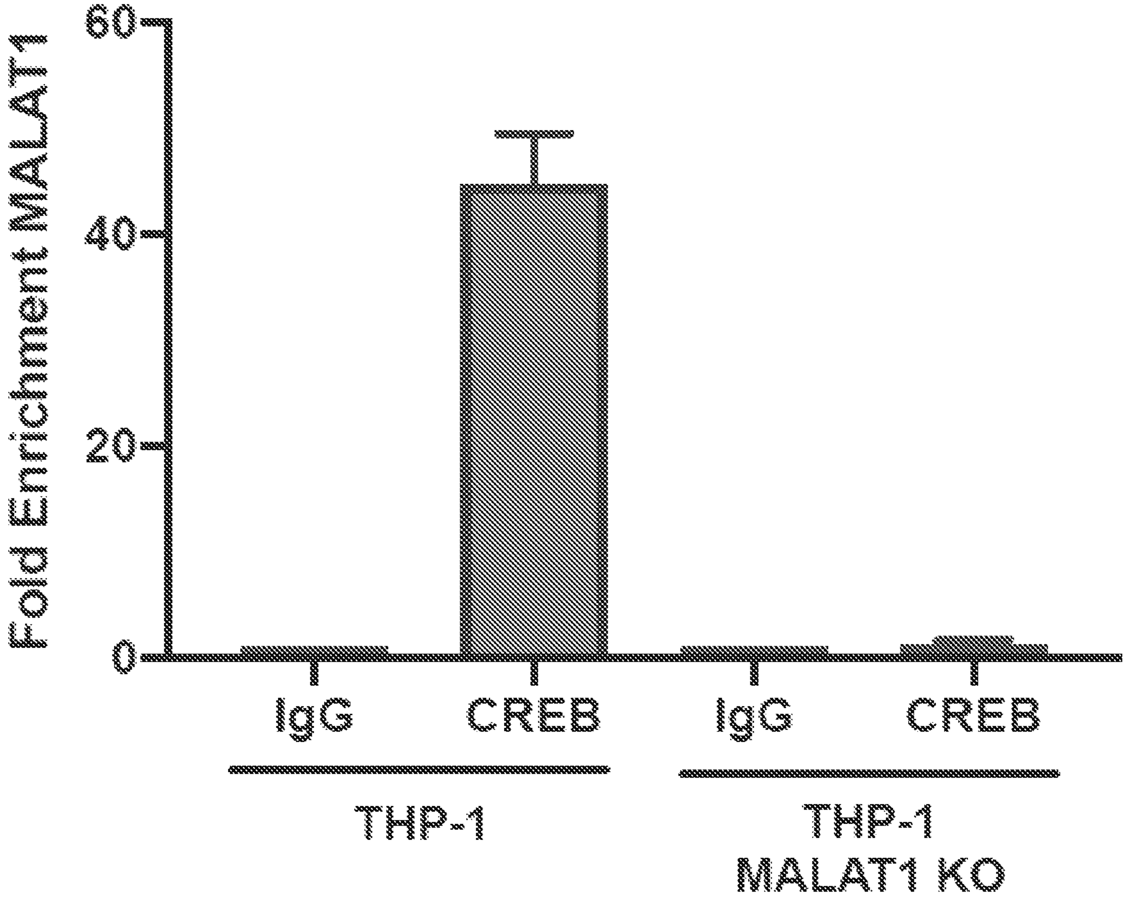
Figure 10F:
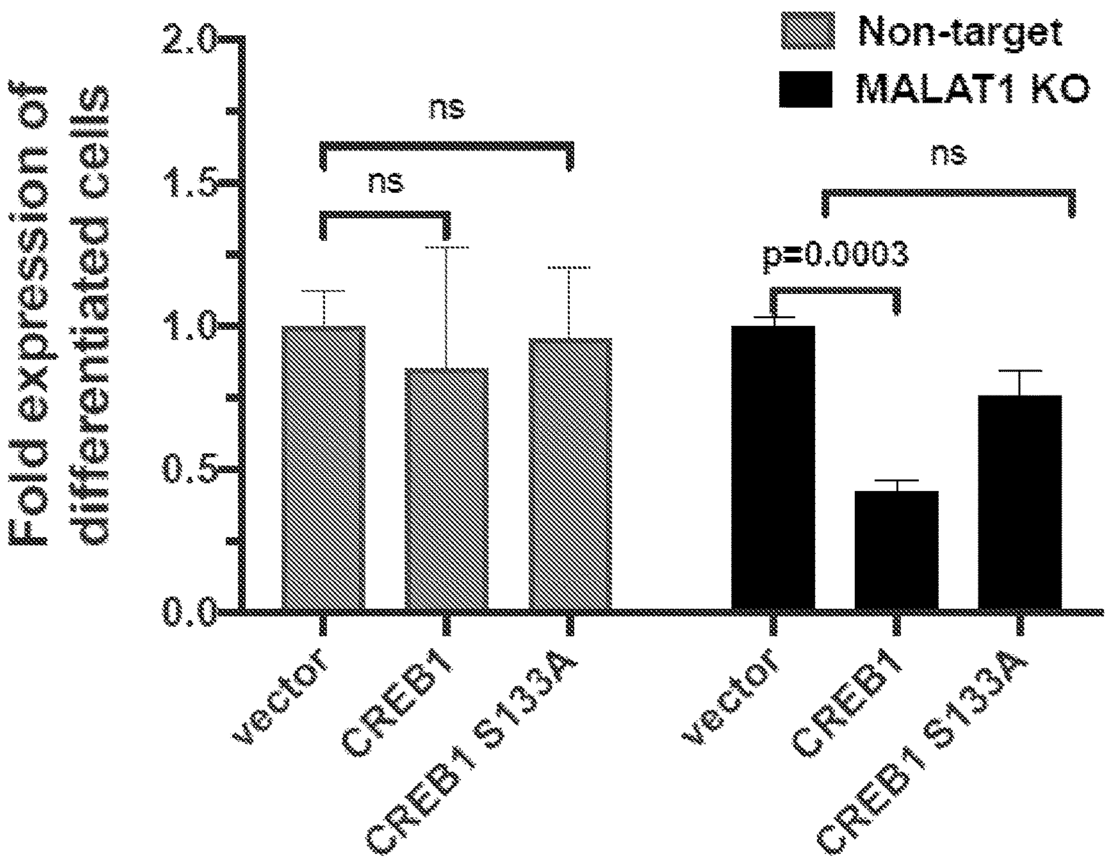

To determine the mechanistic basis for these observations, whole transcriptome RNA sequencing of THP-1 MALAT1 ASO and control treated cells was performed. Given the convergent interaction of transcription factors with both myeloid differentiation and MALAT1, analysis was focused to identify transcriptional signatures that were enriched when comparing MALAT1 depleted versus control cells using the metacore gengo pipeline. As shown in FIG. 10B, 13 statistically significant enrichments were identified across a range of transcription factors. However, the largest enrichment was in genes targeted by the transcription factor CREB. To explore this further, western blot analysis of CREB was performed in human models of MALAT1 depletion. While total CREB and stimulated phosphorylated CREB were unchanged, lower basal levels of serine 133 (S133) CREB phosphorylation was observed in MALAT1 depleted cells compared to controls (FIG. 10C). Consistent with S133's known role in CREB activation, immunofluorescent microscopy identified a statistically significant decrease in nuclear translocation of CREB in MALAT1 depleted cells (FIG. 10D). Further, RNA immunoprecipitation of CREB demonstrated over a 40 fold enrichment of MALAT1 RNA across its entire transcript compared to controls suggesting that MALAT1 and CREB physically interact. Importantly, overexpression of RFP-tagged WT or constitutively active CREB but not its dominant negative (S133A) rescued the differentiation effect seen in ATRA treated MKO cells by flow cytometry (FIG. 10F). Collectively, these data suggest that MALAT1 depletion results in decreased basal phosphorylation and activation of CREB that is sufficient to induce myelomonocytic differentiation.

MALAT1 depletion decreases basal S133 phosphorylation of CREB by increasing its PP2A interaction.

Figure 10G:
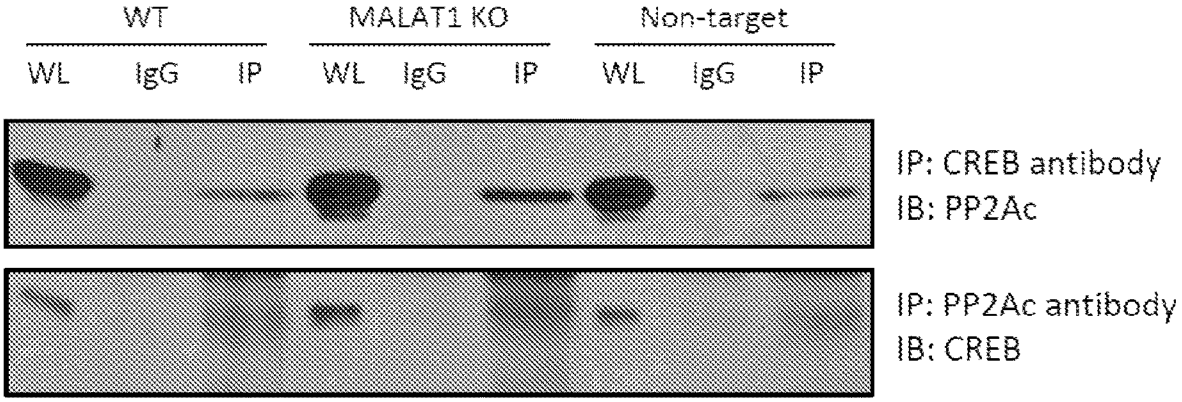

To understand how MALAT1 influences phosphorylation of S133 on CREB, the serine/threonine phosphatase PP2A was focused on for three reasons. First, that basal but not stimulated phosphorylation, which occurs and is measured within minutes to hours, was augmented suggested that a dephosphorylation event may be promoted upon MALAT1 deletion. Second, PP2A is the major phosphatase responsible for dephosphorylating S133 on CREB. Third, a recent study suggested that MALAT1 and PP2A interact in a retinal degeneration murine model. Taken together, it was reasoned that MALAT1 may prevent the CREB PP2A interaction and that MALAT1 depletion may decrease phospho-CREB by restoring this interaction. In support of this hypothesis, immunoprecipitation experiments were performed in THP-1 MALAT1 depleted cells pulling down CREB and blotting with a PP2A antibody and its inverse and demonstrated that MALAT1 depleted cells had higher levels of CREB PP2A interaction compared to controls (FIG. 10G).

Discussion

Overall, these data suggests that MALAT1 expression regulates CREB phosphorylation through its interaction with PP2A leading to differentiation arrest in monocytic leukemia. This is consistent with several studies examining the role of CREB across normal and malignant hematopoiesis. For example, a transgenic mouse overexpressing CREB demonstrated that increased activation of CREB was phenotypically associated with a CMML-like disease and resulted in increased proliferation and survival in vivo and in vitro, respectively. Further, AML myeloblast have been demonstrated to have increased total CREB levels compared to normal controls and CREB expression has been associated with prognosis in AML in retrospective studies. Interestingly, increased CREB activation is associated with HSCs in normal hematopoiesis and with resistance to ATRA in models of acute promyelocytic leukemia (APL) consistent with the data presented here.

Differentiation arrest and an increase in stem and progenitor bone marrow cells is a pathologic hallmark of adult myeloid leukemias including CMML and AML (Petrie, K., et al. Curr Opin Hematol 2009 16:84-91). Efforts to devise pharmacologic agents to promote leukemic differentiation have been among the most successful strategies in leukemia with minimal side effects compared to conventional chemotherapy. The prototypical example of the therapeutic success of differentiation therapy is All-trans Retinoic Acid (ATRA) for the treatment of acute promyelocytic leukemia (APL). Prior to the clinical use of ATRA, APL was a fulminant and lethal leukemia with a 5-year overall survival of 35% (Bernard, J. et al. Blood 1973 41:489-496). However, with the observation that APL cell lines were sensitive to retinoic acid therapy in vitro and the discovery of the PML:RARA gene fusion, ATRA based therapy has resulted in cure rates approaching 95% (Fenaux, P. et al. Blood 1999 94:1192-1200; Tallman, M. S. et al. New England Journal of Medicine 1997 337:1021-1028).

ATRA therapy has been clinically tested in CMML (Cambier, N. et al. Leukemia 1996 10:1164-1167). In a small phase 2 study, 10 CMML patients were treated with 45mg/$m^2$ of ATRA daily. Of these 10 patients, 2 patients developed differentiation syndrome and four patients had improvement in their transfusion requirements. Although 1 of the patients succumbed to differentiation syndrome in this study, these data provide proof-of-concept that ATRA-based therapy may be a viable therapeutic strategy in CMML. Therefore, there remains a critical need to identify novel combination strategies to maximize differentiation and clinical efficacy in lethal diseases such as CMML.

These data nominate the lncRNA MALAT1 as a new regulator of myeloid differentiation through its interaction with CREB and nominates a clinically relevant differentiation therapy for CMML. The lack of phenotypic abnormalities observed in MALAT1$^{KO/KO}$ mice and improvements in antisense oligonucleotide technology suggest a therapeutic window and molecular strategy for such a therapy, respectively.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating chronic myelomonocytic leukemia (CMML) in a subject in need thereof, comprising administering to the subject a therapeutically effective amount of a MALAT1 antisense oligonucleotide or siRNA and a therapeutically effective amount of retinoic acid, wherein the MALAT1 antisense oligonucleotide or siRNA comprises a nucleic acid sequence that is complementary to a contiguous portion of human MALAT1 RNA 14 to 100 base pairs in length.

2. The method of claim 1, wherein the retinoic acid comprises all-trans retinoic acid (ATRA).

3. The method of claim 1, further comprising administering to the subject a therapeutically effective amount of dexamethasone.

4. The method of claim 1, wherein the subject has not received dexamethasone.

5. A composition, comprising a therapeutically effective amount of a MALAT1 antisense oligonucleotide or siRNA and a therapeutically effective amount of retinoic acid, wherein the MALAT1 antisense oligonucleotide or siRNA is complementary to a contiguous portion of human MALAT1 RNA 14 to 100 base pairs in length.

6. The composition of claim 5, wherein the retinoic acid comprises all-trans retinoic acid (ATRA).

7. The composition of claim 5, further comprising a therapeutically effective amount of dexamethasone.

* * * * *